United States Patent
Zeitler et al.

(10) Patent No.: US 9,352,016 B2
(45) Date of Patent: May 31, 2016

(54) FACTOR XII INHIBITORS FOR THE ADMINISTRATION WITH MEDICAL PROCEDURES COMPRISING CONTACT WITH ARTIFICIAL SURFACES

(75) Inventors: Stefan Zeitler, Weil am Rhein (DE); Marc Nolte, Lahntal (DE); Stefan Schulte, Marburg (DE); Gerhard Dickneite, Marburg (DE); Ingo Pragst, Marburg (DE)

(73) Assignee: CSL Behring GmbH, Marburg (DE)

( * ) Notice: Subject to any disclaimer, the term of this patent is extended or adjusted under 35 U.S.C. 154(b) by 0 days.

(21) Appl. No.: 14/004,066

(22) PCT Filed: Mar. 9, 2012

(86) PCT No.: PCT/EP2012/054149
§ 371 (c)(1),
(2), (4) Date: Nov. 18, 2013

(87) PCT Pub. No.: WO2012/120128
PCT Pub. Date: Sep. 13, 2012

(65) Prior Publication Data
US 2014/0072600 A1    Mar. 13, 2014

Related U.S. Application Data

(60) Provisional application No. 61/450,881, filed on Mar. 9, 2011, provisional application No. 61/496,740, filed on Jun. 14, 2011.

(30) Foreign Application Priority Data

Mar. 9, 2011  (EP) ..................................... 11157557

(51) Int. Cl.
| | |
|---|---|
| A61K 9/00 | (2006.01) |
| A61K 36/00 | (2006.01) |
| A61K 38/16 | (2006.01) |
| A61K 38/55 | (2006.01) |
| A61K 38/57 | (2006.01) |
| C07K 16/36 | (2006.01) |
| C07K 16/40 | (2006.01) |
| A61K 31/727 | (2006.01) |
| A61K 38/17 | (2006.01) |
| A61K 47/48 | (2006.01) |

(52) U.S. Cl.
CPC ............. *A61K 38/16* (2013.01); *A61K 31/727* (2013.01); *A61K 38/1767* (2013.01); *A61K 38/556* (2013.01); *A61K 38/57* (2013.01); *A61K 47/48246* (2013.01); *C07K 16/36* (2013.01); *C07K 16/40* (2013.01)

(58) Field of Classification Search
None
See application file for complete search history.

(56) References Cited

U.S. PATENT DOCUMENTS

| | | | |
|---|---|---|---|
| 5,380,299 A | 1/1995 | Fearnot et al. | |
| 6,403,077 B1 | 6/2002 | Strom et al. | |
| 6,613,890 B2 | 9/2003 | White et al. | |
| 8,283,319 B2* | 10/2012 | Schulte et al. | 514/13.7 |
| 2004/0087778 A1 | 5/2004 | Feige et al. | |
| 2005/0059660 A1 | 3/2005 | Fox et al. | |
| 2005/0060028 A1 | 3/2005 | Horres et al. | |
| 2006/0148901 A1 | 7/2006 | Sturzebecher et al. | |
| 2008/0254039 A1* | 10/2008 | Nieswandt et al. | 424/158.1 |
| 2010/0317848 A1 | 12/2010 | Han et al. | |

FOREIGN PATENT DOCUMENTS

| | | |
|---|---|---|
| JP | S5714358 A | 1/1982 |
| JP | 2010518039 A | 5/2010 |
| WO | WO 99/36439 A1 | 7/1999 |
| WO | WO 01/79271 A1 | 10/2001 |
| WO | WO 03/076567 A2 | 9/2003 |
| WO | WO 2004/100982 A1 | 11/2004 |
| WO | WO 2004/101740 A2 | 11/2004 |
| WO | WO 2005/000892 A2 | 1/2005 |
| WO | WO 2005/001025 A2 | 1/2005 |
| WO | WO 2005/024044 A2 | 3/2005 |
| WO | WO 2005/063808 A1 | 7/2005 |
| WO | WO 2006/000448 A2 | 1/2006 |
| WO | WO 2006/066878 A1 | 6/2006 |
| WO | WO 2007/073186 A2 | 6/2007 |
| WO | WO 2008/098720 * | 8/2008 |
| WO | WO 2008/098720 A1 | 8/2008 |
| WO | WO 2009/067660 A2 | 5/2009 |

OTHER PUBLICATIONS

Stutz (Scientific American, Jan. 9, 2009, retrieved online on Sep. 23, 2014 from URL:<http://www.scientificamerican.com/article/pumphead-heart-lung-machine/>.*
Buchwald et al, Platelet and Fibrin Deposition on Coronary Stents in Minipigs: Effect of Hirudin Versus Heparin (J Am Coll Cardiol. Jan. 1993;21(1):249-54).*
Briguori et al, Administration of protamine after coronary stent deployment (Am Heart J 1999;138:64-8).*
Moskowitz et al, Use of the Hemobag for Modified Ultrafiltration in a Jehovah's Witness Patient Undergoing Cardiac Surgery (JECT. 2006;38:265-270).*
Bauer et al, Prevalence of Heparin-Associated Antibodies Without Thrombosis in Patients Undergoing Cardiopulmonary Bypass Surgery (Circulation. 1997; 95: 1242-1246).*

(Continued)

*Primary Examiner* — James H Alstrum Acevedo
*Assistant Examiner* — Sergio Coffa
(74) *Attorney, Agent, or Firm* — Finnegan, Henderson, Farabow, Garrett & Dunner LLP

(57) ABSTRACT

An inhibitor of FXII/FXIIa for the prevention of the formation and/or stabilization of thrombi during and/or after a medical procedure performed on a human or animal subject comprising contacting blood of said human or animal subject with artificial surfaces, wherein said inhibitor of FXII/FXIIa is administered before and/or during and/or after said medical procedure.

17 Claims, 10 Drawing Sheets

(56) References Cited

OTHER PUBLICATIONS

Beattie, W. et al.; "Structure and evolution of human α-fetoprotein deduced from partial sequence of cloned cDNA"; Gene; vol. 20; 1982; pp. 415-422.

Campos, I.T.N. et al.; "Infestin, a thrombin inhibitor presents in *Triatoma infestans* midgut, a Chagas' disease vector: gene cloning, expression and characterization of the inhibitor"; Insect Biochem. Mol. Bio.; vol. 32; 2002; pp. 991-997.

Campos, I.T.N. et al.; "Identification and characterization of a novel factor XIIa inhibitor in the hemato-phagous insect, *Triatoma infestans* (Hemiptera: Reduviidae)"; FEBS Lett.; vol. 577; 2004; pp. 512-516.

Chen,. Z.Y. et al.; "Inhibition of Plant-Pathogenic Fungi by a Corn Trypsin Inhibitor Overexpressed in *Escherichia coli*"; Applied and Environmental Microbiology; vol. 65, No. 3; Mar. 1999; pp. 1320-1324.

Cooke, E. et al.; "Serum Vitamin D-binding Protein is a Third Member of the Albumin and Alpha Fetoprotein Gene Family"; J. Clin. Invest.; vol. 76; Dec. 1985; pp. 2420-2424.

Devereux, J. et al.; "A comprehensive set of sequence analysis programs for the VAX"; Nucleic Acids Research; vol. 12, No. 1; 1984; pp. 387-395.

Dyke, C. et al.; "Preemptive Use of Bivalirudin for Urgent On-Pump Coronary Artery Bypass Grafting in Patients With Potential Heparin-Induced Thrombocytopenia"; Ann. Thorac. Surg.; vol. 80; 2005; pp. 299-303.

Gruenwald, C. et al.; "Management and Monitoring of Anticoagulation for Children Undergoing Cardiopulmonary Bypass in Cardiac Surgery"; The Journal of Extra Corporeal Technology; vol. 42; 2010; pp. 9-19.

Isawa, H. et al.; "A mosquito salivary protein inhibits activation of the plasma contact system by binding to factor XII and high molecular weight kininogen"; J. Biol. Chem.; vol. 277, No. 31; Aug. 2, 2002; pp. 27651-27658.

Kibbe, A., et al.; "Handbook of Pharmaceutical Excipients"; Third Edition; Pharmaceutical Press; London; 2000; book review, in J. Controlled Release; vol. 71; 2001; pp. 352-352.

Koster, A. et al.; "Effectiveness of *Bivalirudin* as a Replacement for *Heparin* During Cardiopulmonary Bypass in Patients Undergoing Coronary Artery Bypass Grafting"; Am. J. Cardio.; vol. 93; Feb. 1, 2004; pp. 356-359.

Laskowski, M. et al.; "Protein Inhibitors of Proteinases"; Ann. Rev. Biochem.; vol. 49; 1980; pp. 593-626.

Lichenstein, H. et al.; "Afamin Is a New Member of the Albumin, α-Fetoprotein, and Vitamin D-binding Protein Gene Family"; J. Biol. Chem.; vol. 269, No. 27; Jul. 8, 1994; pp. 18149-18154.

Mackman N.; "Role of tissue factor in hemostasis, thrombosis, and vascular development"; Arterioscler. Thromb. Vasc. Biol.; vol. 24; 2004; pp. 1015-1022.

Newman, M. et al.; "Longitudinal Assessment of Neurocognitive Function After Coronary-artery Bypass Surgery"; NEJM; vol. 344, No. 6; Feb. 8, 2001; pp. 395-402.

Ravon, D. et al., "Monoclonal antibody F1 Binds to the Kringle Domain of Factor XII and Induces Enhanced Susceptibility for Cleavage by Kallikrein"; Blood; vol. 86, No. 11; Dec. 1, 1995; pp. 4134-4143.

Renne, T. et al.; "Defective thrombus formation in mice lacking factor XII"; J. Exp. Med.; vol. 202, No. 2; Jul. 18, 2005; pp. 271-281.

Sperling, C. et al.; "Blood coagulation on biomaterials requires the combination of distinct activation processes"; Biomaterials; vol. 30; 2009; pp. 4447-4456.

Wen, L. et al.; "Nucleotide sequence of a cDNA clone that encodes the maize inhibitor of trypsin and activated Hageman factor"; Plant Molecular Biology; vol. 18; 1992; pp. 813-814.

Wendel, H.P. et al.; "Influence of heparin, heparin plus aprotinin and hirudin on contact activation in a cardiopulmonary bypass model"; Immunopharmacology; vol. 32; 1996; pp. 57-61.

Wendel, H.P. et al.; "Heparin-coated devices and high-does aprotinin optimally inhibit contact system activation in an in vitro cardiopulmonary bypass model"; Immunopharmacology; vol. 32; 1996; pp. 128-130.

Werle, M. et al.; "Strategies to improve plasma half life time of peptide and protein drugs"; Amino Acids; vol. 30; 2006; pp. 351-367.

Williams, A. et al.; "DX-88 and HAE: a developmental perspective"; Transfus. Apheresis Sci.; vol. 29; 2003; pp. 255-258.

Yu, J. et al.; "Polymeric biomaterials: influence of phosphorylcholine polar groups on protein adsorption and complement activation"; Int. J. Artif. Organs; vol. 17, No. 9; 1994; pp. 499-504.

International Search Report and Written Opinion dated Apr. 18, 2012; International Application No. PCT/EP2012/054149 filed Mar. 9, 2012; 12 pages.

Extended European Search Report dated Sep. 19, 2011; European Application No. 11157557.7; 11 pages.

Chinese Office Action for Chinese Patent Application No. 201280012244.0, dated Sep. 24, 2014, with English translation (20 pages).

Edmunds et al, "Thrombin During Cardiopulmonary Bypass," *Ann. Thorac. Surg.*, 82:2315-2322 (2006).

Kleinschnitz et al., "Targeting coagulation factor XII provides protection from pathological thrombosis in cerebral ischemia without interfering with hemostasis ," *The Journal of Experimental Medicine*, 203(3): 513-518 (2006).

Koster et al., "Anticoagulation in Cardiac Surgery," *Hemostasis*, $2^{nd}$ Edition, 638-645 (2010). Machine Translation.

Kuijpers et al., "Factor XII Regulates the Pathological Process of Thrombus Formation on Ruptured Plaques," *Arterioscler. Thromb. Vasc. Bio.*, 34: 1674-1680 (2014).

Giles et al., "The Thrombogenicity of Prothrombin Complex Concentrates," *Thrombosis Research* (1980) 17:353-366.

Larsson et al., "A Factor XIIa Inhibitory Antibody Provides Thromboprotection in Extracorporeal Circulation Without Increasing Bleeding Risk," *Science Translational Medicine*, (2014) 6(222):222ra17.

Sander and Giles, "Ximelagatran: Light at the end of the tunnel or the next tunnel?" *Am J Geriatr Cardiol*, (2004) 13(4).

Schmaier, "Extracorporeal Circulation Without Bleeding," *Science Translational Medicine*, (2014) 6(222):222fs7.

Wessler et al., "Studies in Intravascular Coagulation," *J Clin Invest* (1955) 34(4):647-651.

Hagedorn et al., "Factor XIIa Inhibitor Recombinant Human Albumin Infestin-4 Abolishes Occlusive Arterial Thrombus Formation Without Affecting Bleeding," Circulation, 2010; 121(13): 1510-1517.

Japanese Office Action for Japanese Patent Application No. 2013-557120, dated Dec. 1, 2015, English Translation only (4 pages).

* cited by examiner

Figure 1 – Ex vivo WBCT of porcine whole blood:
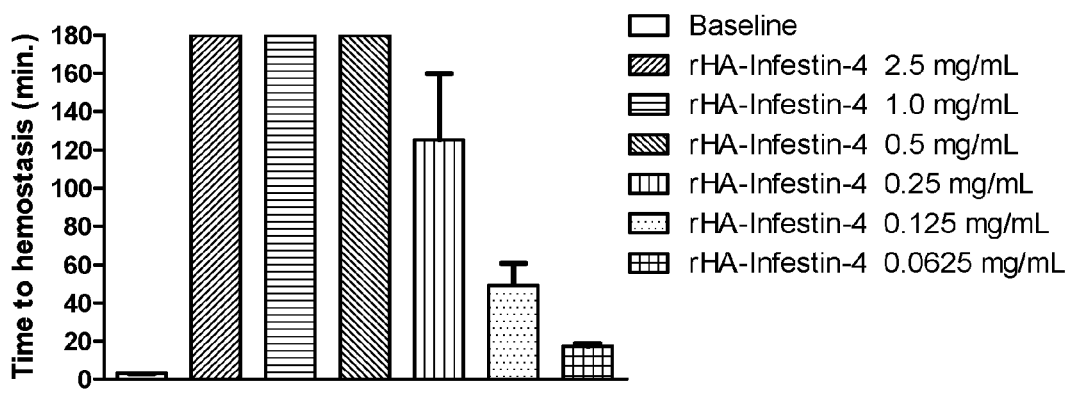
Figure 2 – Ex vivo WBCT of murine whole blood:
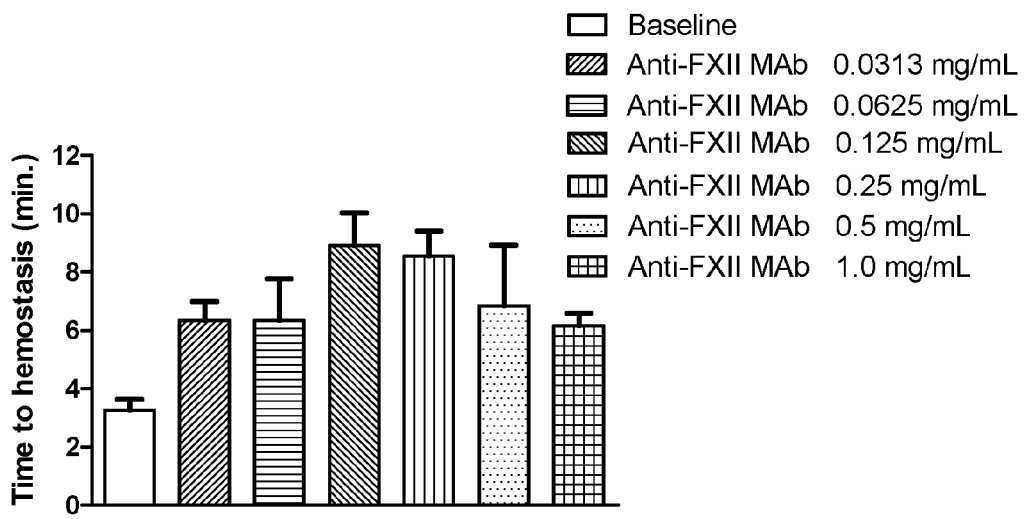

Figure 3 – Ex vivo WBCT of porcine whole blood (rHA-Infestin-4):
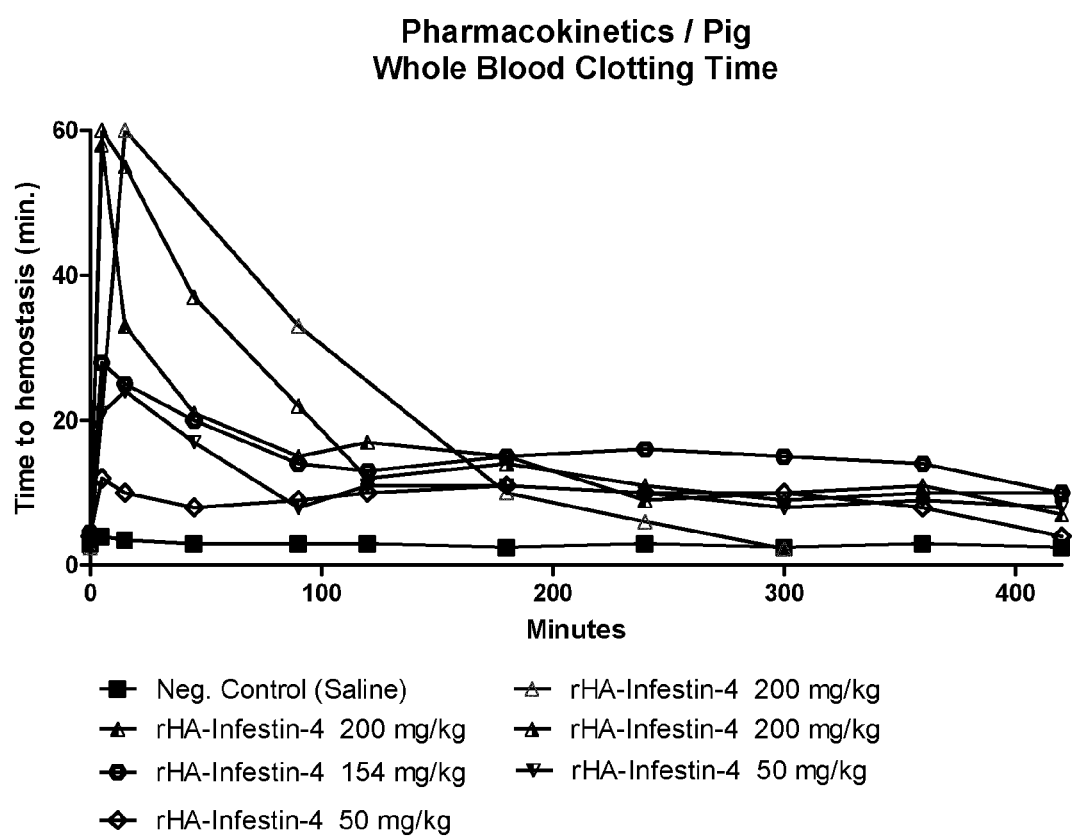

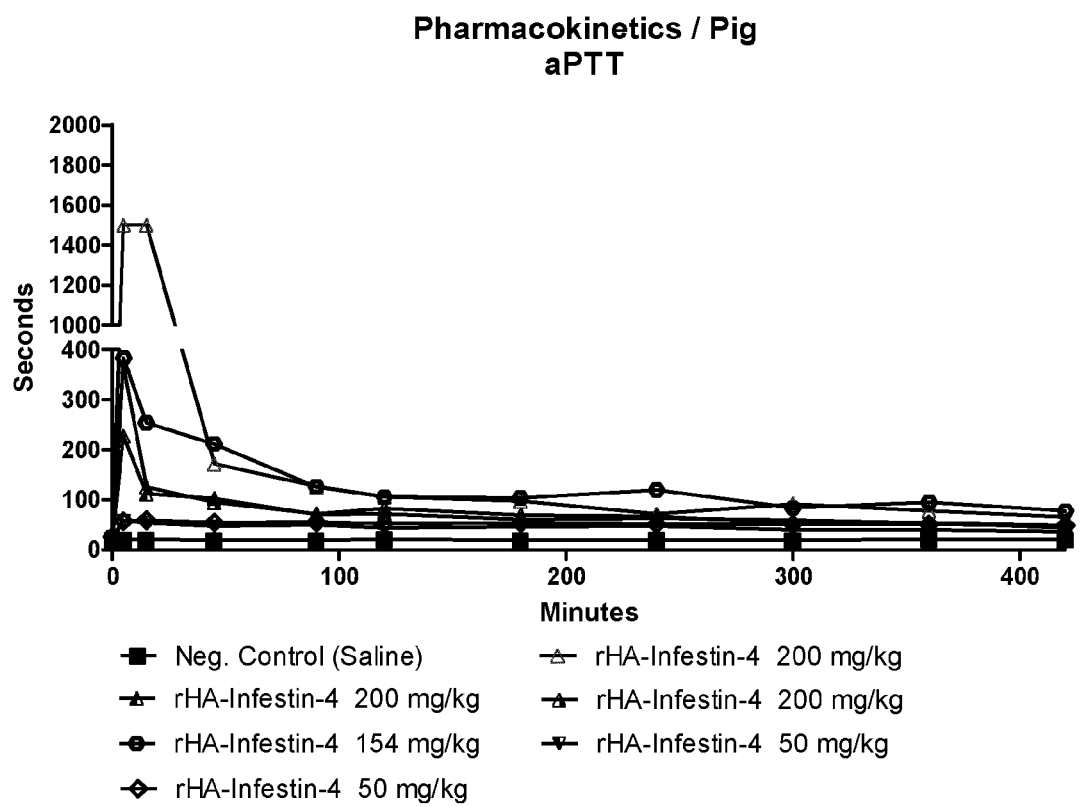
Figure 4 – Ex vivo aPTT measurement of porcine blood (rHA-Infestin-4):

Figure 5 – Ex vivo PT measurement of porcine blood (rHA-Infestin-4):
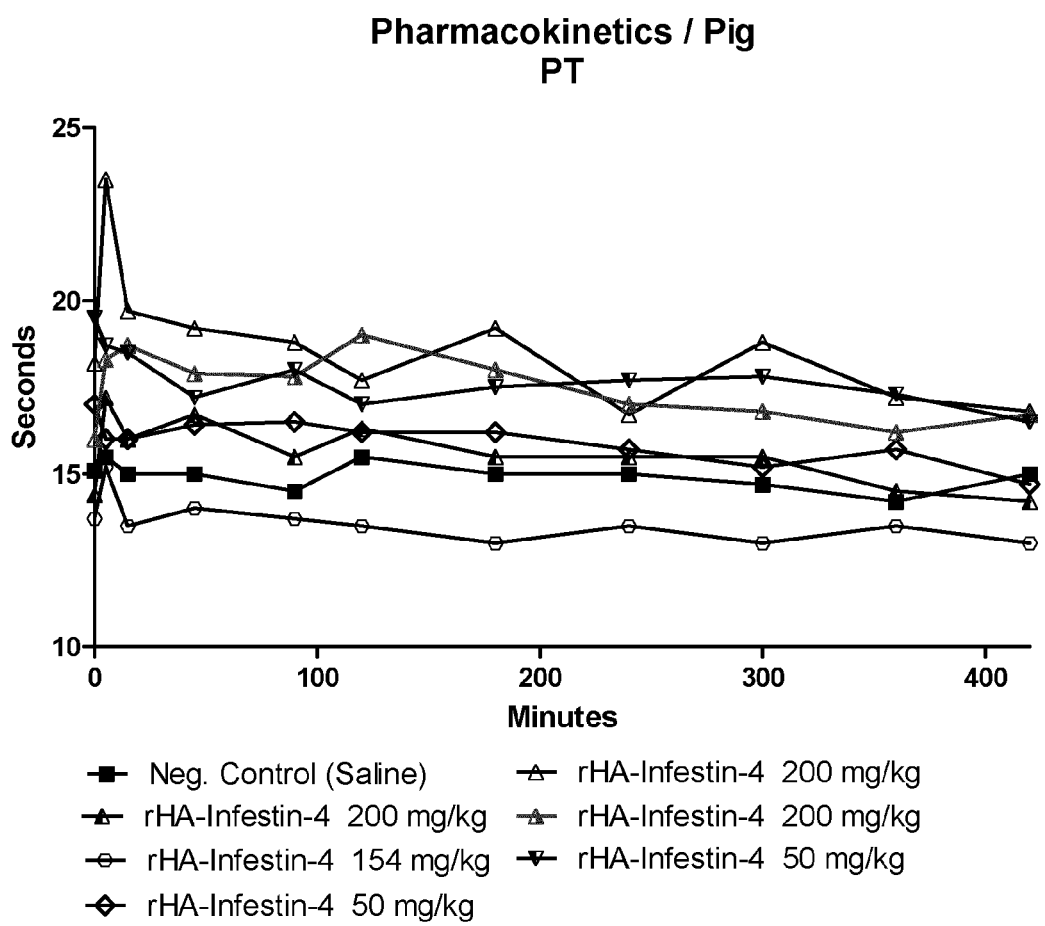

Figure 6 – Porcine skin bleeding time (rHA-Infestin-4):
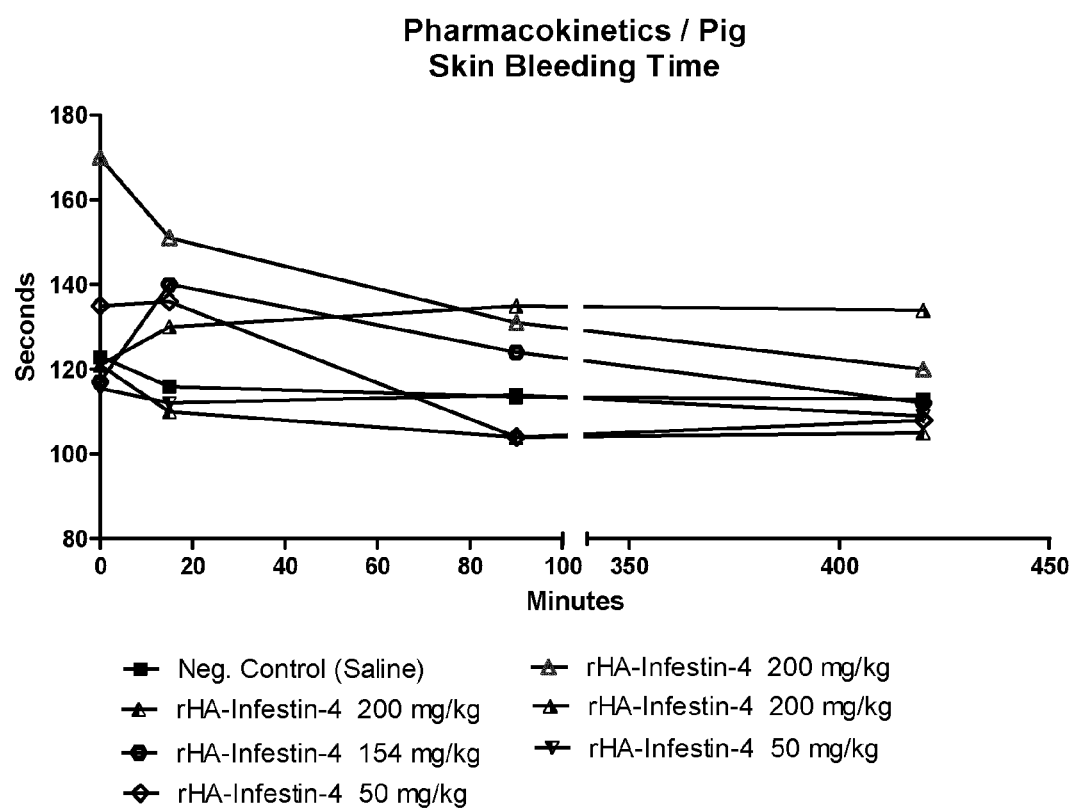

Figure 7 – Extracorporeal circulation in pig – study design:
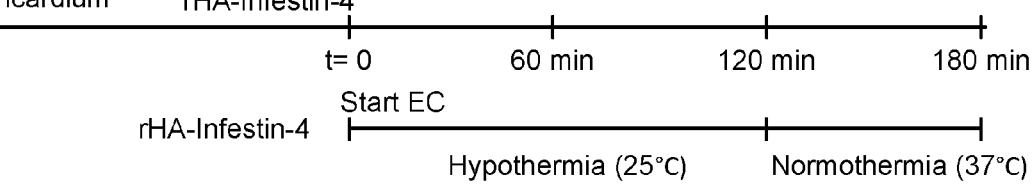

Figure 8 – Extracorporeal circulation in pig – aPTT:
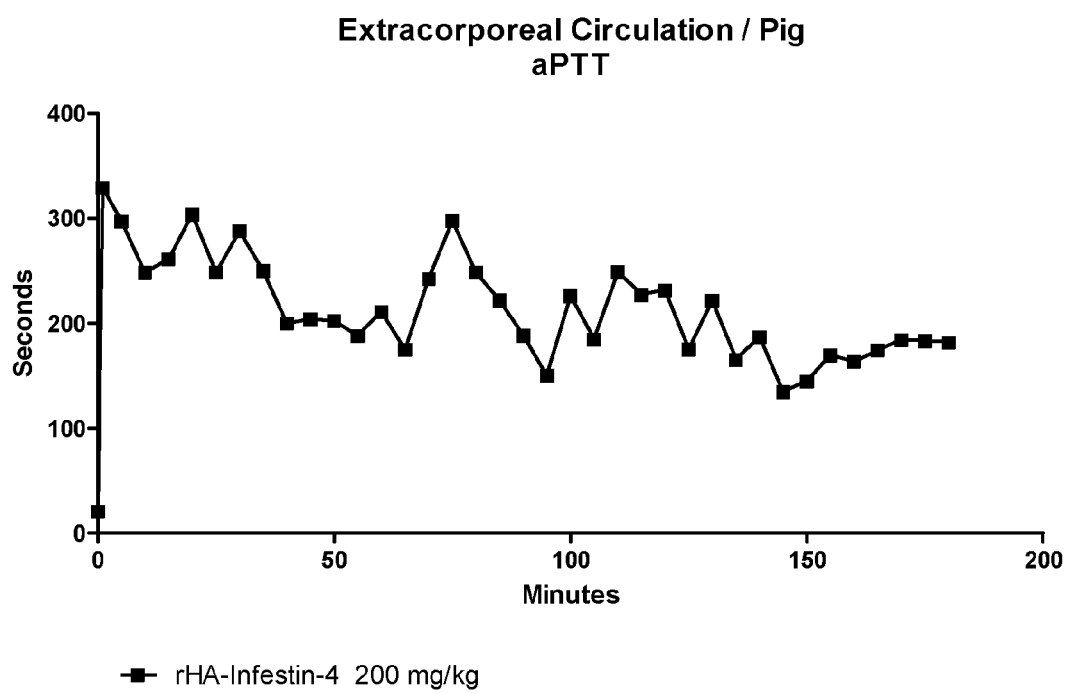

Figure 9 – Extracorporeal circulation in pig – PT:
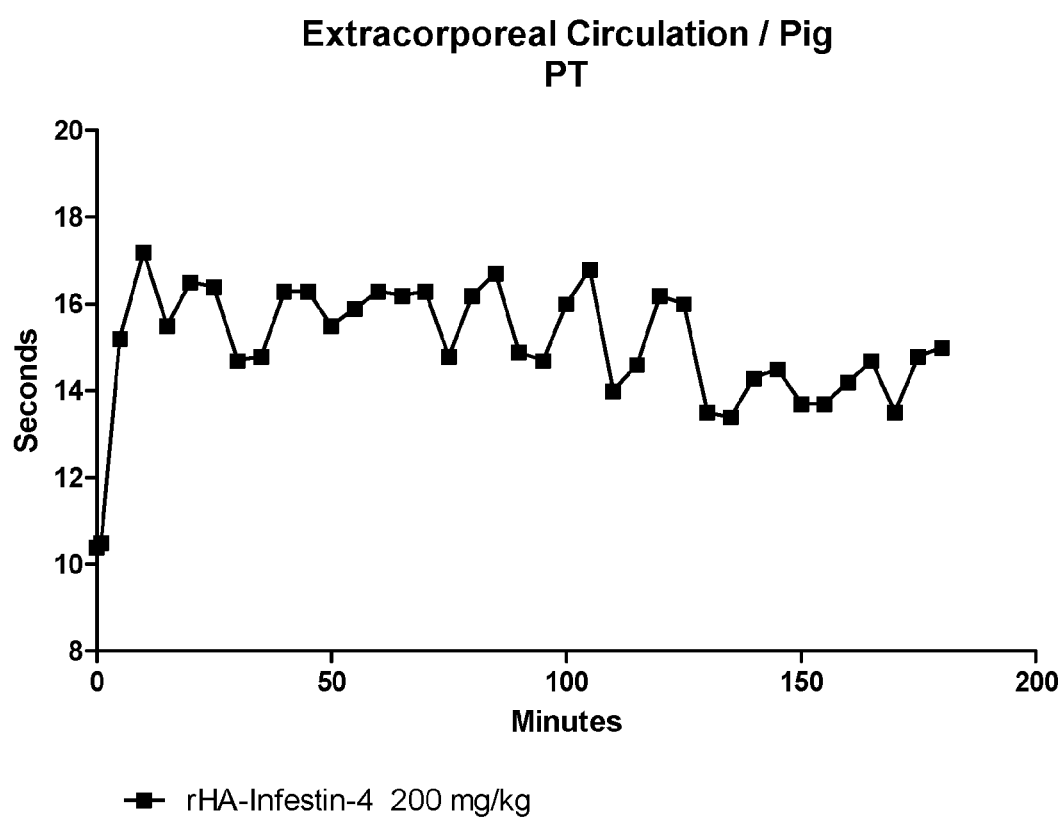

Figure 10 – Extracorporeal circulation in pig – whole blood clotting time:

```
        ###        #######     # ##                    # #
Rho  EGGEPC-----ACPHALHRVCGSDGETYSNPCTLNCAKFNGKPELVKVHDGPC
I4   EVRNPC-----ACFRNYVPVCGSDGKTYGNPCMLNCAAQTKVPGLKLVHEGRC
SP   GREAKCYNELNGCTKIYDPVCGTDGNTYPNECVL-CFENRKRTSILIQKSGPC
            +++++++++++++         ++   +     +
```

Figure 12

* denotes identical; | denotes similar amino acid; bold amino acids are conserved cysteines; underlined amino acids 2-13 of the Infestin-4 sequence are conserved.

```
              1    5         10   15   20   25   30   35   40   45
I4              EVRNPC-----ACFRNYVPVCGSDGKTYGNPCMLNCAAQTKVPGLKLV-HEGRC
                * | *      * | * ****|** ** * *|* *   | *     *|   * *
SP:    DSLGREAK--CYNELNGCTKIYDPVCGTDGNTYPNECVL-CFENRKRQTSILIQKSGPC
       1    5         10   15   20   25   30   35   40   45   50   55
```

Figure 13

* denotes identical; | similar amino acids with regard to the Infestin-4 sequence. Underlined amino acids in I4 were used to replace SP amino acids. Underlined amino acids in K2 and K3 are additional point mutations on the K1 sequence.

```
I4         EVRNPC-----ACFRNYVPVCGSDGKTYGNPCMLNCAAQTKVPGLKLV-HEGRC
SP: DSLGREAK--CYNELNGCTKIYDPVCGTDGNTYPNECVL-CFENRKRQTSILIQKSGPC
            * | *      * | * ****|** ** * *|* *   | *     *|   * *
K1: DSLGREVRNPC-----ACFRNYVPVCGTDGNTYPNECVL-CFENRKRQTSILIQKSGPC
           ******     **********|** ** * *|* *   | *     *|   * *
K2: DSLGREVRNPC-----ACFRNYVPVCGTDGNTYGNECML-CAENRKRQTSILIQKEGPC
           ******     **********|** **** *** **  | *     *|   ** *
K3: DSLGREVRNPC-----ACFRNYVPVCGTDGNTYGNECMLNCAENRKRQTSILIQKEGPC
           ******     **********|** **** ******  | *     *|   ** *
```

FACTOR XII INHIBITORS FOR THE ADMINISTRATION WITH MEDICAL PROCEDURES COMPRISING CONTACT WITH ARTIFICIAL SURFACES

This application is the United States national stage of PCT/EP2012/054149, filed Mar. 9, 2012, (published as WO 2012/120128), and also claims priority to European Patent Application No. 11 157 557.7, filed Mar. 9, 2011, U.S. Provisional Application No. 61/450,881, filed Mar. 9, 2011, and U.S. Provisional Application No. 61/496,740, filed Jun. 14, 2011, all of which are incorporated herein by reference.

FIELD

The present application relates to the use of inhibitors of FXII/FXIIa in medical procedures which comprise contacting blood with artificial surfaces. Certain embodiments relate to the anticoagulant therapy of patients who need surgical procedures that call for cardiopulmonary bypass (CPB) pumps where the novel use of coagulation factor FXII/FXIIa inhibitors reduces or replaces the need for heparin/bivalirudin administration during CPB procedures. In certain embodiments, the FXII inhibitor is coated on the artificial surface.

BACKGROUND

Vessel wall injury and artificial surfaces trigger sudden adhesion and aggregation of blood platelets, followed by the activation of the plasma coagulation system and the formation of fibrin-containing thrombi, which occlude the site of injury. These mechanisms are crucial to limit post-traumatic blood loss but may also occlude diseased vessels leading to ischemia and infarction of vital organs, or occlusion of CPB membranes.

In the classical waterfall model, blood coagulation proceeds by a series of reactions involving the activation of zymogens by limited proteolysis culminating in generation of thrombin, which converts plasma fibrinogen to fibrin and activates platelets. In turn, collagen- or fibrin-adherent platelets facilitate thrombin generation by several orders of magnitude via exposing procoagulant phospholipids (mainly phosphatidyl serine) on their outer surface, which propagates assembly and activation of coagulation protease complexes and by direct interaction between platelet receptors and coagulation factors.

Two converging pathways for coagulation exist that are triggered by either extrinsic (vessel wall) or intrinsic (blood-borne) components of the vascular system. The "extrinsic" pathway is initiated by the complex of the plasma factor VII (FVII) with the integral membrane protein tissue factor (TF), an essential coagulation cofactor that is absent on the luminal surface but strongly expressed in subendothelial layers of the vessel and which is accessible or liberated via tissue injury. TF expressed in circulating microvesicles might also contribute to thrombus propagation by sustaining thrombin generation on the surface of activated platelets.

The "intrinsic" or "contact activation pathway" is initiated when factor XII (FXII, Hageman factor) comes into contact with negatively charged surfaces in a reaction involving high molecular weight kininogen and plasma kallikrein. FXII can be activated by macromolecular constituents of the subendothelial matrix such as glycosaminoglycans and collagens, sulfatides, nucleotides and other soluble polyanions or non-physiological material such as glass or polymers. One of the most potent contact activators is kaolin and this reaction serves as the mechanistic basis for the major clinical clotting test, the activated partial thromboplastin time (aPTT), which measures the coagulation function of the "intrinsic" pathway. In reactions propagated by platelets, activated FXII (FXIIa) then activates FXI to FXIa and subsequently FXIa activates FIX to FIXa. The complex of FVIIIa, which FVIIIa has been previously activated by traces of FXa and/or thrombin, and FIXa (the tenase complex) subsequently activates FX to FXa. Despite its high potency to induce blood clotting in vitro, the (patho-) physiological significance of the FXII-triggered intrinsic coagulation pathway is questioned by the fact that hereditary deficiencies of FXII as well as of high molecular weight kininogen and plasma kallikrein are not associated with severe bleeding complications. Together with the observation that humans and mice lacking extrinsic pathway constituents such as TF and FVII suffer from severe bleeding this has led to the current hypothesis that for the cessation of bleeding in vivo exclusively the extrinsic cascade may be required (Mackman, N. 2004. Role of tissue factor in hemostasis, thrombosis, and vascular development. Arterioscler. Thromb. Vasc. Biol. 24, 101 5-1 022).

In pathological conditions, the coagulation cascade may be activated inappropriately which then results in the formation of hemostatically acting plugs inside the blood vessels. Thereby, vessels can be occluded and the blood supply to distal organs is limited. Furthermore, formed thrombi can detach and embolize into other parts of the body, there leading to ischemic occlusion. This process is known as thromboembolism and is associated with high mortality.

In WO20061066878, the use of antibodies against FXII/FXIIa or the use of inhibitors of FXII/FXIIa is proposed to prevent the formation and/or stabilization of thrombi. As potential inhibitors antithrombin (AT III), angiotensin converting enzyme inhibitor, C1 inhibitor, aprotinin, alpha-I protease inhibitor, antipain ([(S)-I-Carboxy-2-Phenylethyl]-Carbamoyl-L-Arg-L-Val-Arginal), Z-Pro-Proaldehyde-dimethyl acetate, DX88 (Dyax Inc., 300 Technology Square, Cambridge, Mass. 02139, USA; cited in: Williams A and Baird LG.2003. DX-88 and HAE: a developmental perspective. *Transfus Apheresis* Sci. 29:255-258), leupeptin, inhibitors of prolyl oligopeptidase such as Fmoc-Ala-Pyr-CN, corn-trypsin inhibitor, mutants of the bovine pancreatic trypsin inhibitor, ecotin, yellowfin sole anticoagulant protein, *Cucurbita maxima* trypsin inhibitor-v including Curcurbita maxima isoinhibitors and Hamadarin (as disclosed by Isawa H et al. 2002. A mosquito salivary protein inhibits activation of the plasma contact system by binding to factor XI and high molecular weight kininogen. J. Biol. Chem. 277:27651-27658) have been proposed.

Recently, Infestin-4 was reported to be a novel inhibitor of FXIIa. Infestins are a class of serine protease inhibitors derived from the midgut of the hematophagous insect, *Triatoma infestans*, a major vector for the parasite Trypanosoma cruzi, known to cause Chagas' disease (Campos ITN et al. 32 *Insect Biochem. Mol. Bio*. 991-997, 2002; Campos ITN et al. 577 *FEBS Lett*. 512-516, 2004). This insect uses these inhibitors to prevent coagulation of ingested blood. The Infestin gene encodes 4 domains that result in proteins that can inhibit different factors in the coagulation pathway. In particular, domain 4 encodes a protein (Infestin-4) that is a strong inhibitor of FXIIa. Infestin-4 has been administered in mice without bleeding complications (WO 2008/098720).

Because artificial surfaces can trigger the contact activation pathway there is a considerable medical risk involved in medical procedures which involve contacting blood with such artificial surfaces. Therefore the use of prosthetic devices or hemodialysers, which come into contact with blood, is severely limited because of activation of the intrinsic coagulation cascade. Suitable coating of the prosthetic surface may avoid said problem in some cases but may compromise its function in others. Examples of such prosthetic devices are heart valves, vascular stents and in-dwelling catheters.

In cases where such devices are used, anticoagulants, such as heparin, need to be administered to prevent fibrin formation on the surface.

However, some patients are intolerant of heparin, which can cause heparin-induced thrombocytopenia (HIT) resulting in platelet aggregation and life-threatening thrombosis. Furthermore, an inherent disadvantage of all anticoagulants used in clinics is an increased risk of serious bleeding events. Therefore, a strong need for new types of anticoagulants exist, which are not associated with such complications and that can be used in affected patients or as superior therapy concept preventing thrombosis without increased bleeding risks (Renne T et al. 2005. Defective thrombus formation in mice lacking factor XII. J. Exp. Med. 202:271-281).

A medical procedure involving a massive contact activation is cardiopulmonary bypass (CPB). Currently CPB devices in cardiac surgery are used for two reasons: a) artificial maintenance of the blood circulation during cardioplegia of patients undergoing heart surgery (pump function) and b) artificial oxygenation of the blood during cardioplegia of patients undergoing heart surgery (oxygenator function) via semipermeable membrane oxygenation.

Due to the artificial blood flow maintenance via the pump function the patient's blood is routed over a semipermeable membrane (~3 m$^2$, artificial surface) that allows oxygen passing through the membrane and binding to erythrocytes while the blood itself keeps in the closed artificial circulation system. This artificial oxygenation is vital to the patient and requires an anticoagulation strategy during CPB (H. P. Wendl at al 1996; Immunpharmacology; C. Sperling et al.; Biomaterials 30 (2009)). The currently used CPB devices have up to 3 m$^2$ artificial surface that leads to a massive contact activation of the coagulation system, the inflammation system as well as activation of the complement system. In order to minimize these effects on the mentioned cascade systems, polymeric biomaterials of different kind are used (e.g. 2-methylacryloxyethylphosphorylcholin MCP) (Yu J et al.; Int J Artif Organs 1994; 17: 499-504; C. Sperling et al. Biomaterial 30 (2009) 4447-4456). Despite the fact that novel surface materials like polar phosphorylcholin which are less thrombogenic are used, it still remains necessary to anticoagulate patients undergoing CPB via heparin/bivalirudin since a platelet-mediated reaction would immediately lead to an occlusion of the CPB oxygenator with fatal outcome for the patient.

Currently there are two products licensed for anticoagulation during CPB:

a) Heparin:

Heparin is administered in body weight adjusted manner (300-400 IU/kg body weight (BW)) to the patient shortly before connecting the CPB devices in order to prevent the patient's blood from clotting. The CPB itself is also loaded with heparin before it is connected to the patient. This is the only anticoagulation strategy that allows CPB operations with an artificial oxygenation during the whole procedure without immediate fatal outcome for the patient. During this procedure the clotting capacity is monitored via activated clotting time (ACT) during the surgery (normal value 100-120 sec.; 300-500 sec. during operation). By measuring the ACT the physician can guide dosing of heparin in a semi-quantitative manner. Heparin binds AT (ATIII) and builds a fast inhibition complex that inactivates the coagulation system. Low molecular weight heparins (LMWH) mainly inhibit the prothrombinase-complex (factor X, factor Va, Ca$^{2+}$, phospholipids) while unfractionated heparins (UFH) also inhibit factor II and therefore react faster than the LMWH. Furthermore, the factors IX, XI, XII and kallikrein are inactivated via heparins.

After the CPB the effect of heparin needs to be antagonized via protamine (1 mg/100 IU heparin) since a potential bleeding event might have a fatal outcome for the patient.

The major limitations of this standard of care are:

i) The amount of heparin in the patient's blood does not correlate with ACT (Gruenwald et al. 2010; the Journal of Extra Corporeal Technology) therefore it remains a risk for the patient to be either in a hypo- or hypercoagulopathic status.

ii) Heparin can induce thrombocypenia (HIT 1, caused by heparin via direct activation of thrombocytes, or HIT 2 caused by heparin and platelet factor 4 accumulations and consecutive development of antibodies against the complexes).

iii) The time window between heparin antagonization after CPB and the beginning of the anticoagulant therapy of patients on an intensive care unit (ICU) remains a risk factor for either bleeding, or thrombotic events.

iv) Protamine as antidote for the effect of heparin itself increases the risk for thrombotic events, severe allergic reactions and fatal drops of blood pressure. Further on a second administration of protamine in case of under dosing might have a fatal outcome for the patient.

b) Bivalirudin:

Bivalirudin (derived from hirudin) is registered for the use in patients with known HIT as an alternative to anticoagulation via heparin. The limitations of this alternative therapy are:

i) No clinical registered antidote in case of bleeding is available at the moment.

ii) Higher consumption of blood products during CPB with resulting postoperative risks (C. Dyke et al.; surgery for acquired cardiovascular disease 2005)

In the present application it was surprisingly found that the use of inhibitors of FXII/FXIIa prevents clotting, while the risk for bleeding during and after CPB procedures is not enhanced in medical procedures which comprise contacting the blood of a patient with artificial surfaces, which in certain embodiments are outside of the body. Therefore only a reduced amount of other anticoagulants in addition to the FXII/FXIIa inhibitor needs to be administered. In one embodiment, the addition of other anticoagulants in addition to the FXII/FXIIa inhibitor can be completely avoided. This leads to safer medical procedures, as the increased bleeding risk which is inherent in the current therapy as well as complications by reversing the anticoagulation are avoided.

SUMMARY OF CERTAIN EMBODIMENTS

The application provides an inhibitor of FXII/FXIIa for use in the prevention of the formation and/or stabilization of thrombi during and/or after a medical procedure performed on a human or animal subject comprising contacting blood of said human or animal subject with artificial surfaces, wherein said inhibitor of FXII/FXIIa is administered before and/or during and/or after said medical procedure. In certain embodiments the contact between said subject's blood and the artificial surface occurs outside of the subject's body. In one embodiment of the invention, the artificial surface is exposed to at least 80%, 90%, or 100% of the blood of the human or animal subject. In another embodiment, the volume of 80%, 90%, or 100% of the blood of the human or animal subject contacts the artificial surface in less than 30 minutes, less than 15 minutes, less than 10 minutes, or less than 5 minutes. In another embodiment, the artificial surface serves as a container for blood outside of the human or animal body, and such blood may be in the amount of at least 50 mL, 100 mL, 200 mL, 300 mL, 400 mL, 500 mL or more. In one embodiment, the artificial surface being exposed to the patient's blood is at least 0.2 m². In embodiments, the artificial surface area is at least 0.1 m², or at least 0.5 m². In another embodiment, the artificial surface excludes retractors, needles, scalpels and other routine surgical equipment that only come in contact with a fraction of a subject's blood.

Another embodiment includes, an Inhibitor of FXII/FXIIa for use in the prevention of the formation and/or stabilization of thrombi during and/or after a medical procedure performed on a human or animal subject comprising contacting blood of said human or animal subject with artificial surfaces, wherein said inhibitor of FXII/FXIIa is administered before and/or during and/or after said medical procedure, and further wherein
 (i) the artificial surface is exposed to at least 80% of the blood volume of the subject and the artificial surface is at least 0.2 m² or
 (ii) the artificial surface is a container for collection of blood outside the body of the subject or
 (iii) the artificial surface is a stent, valve, intraluminal catheter, or a system for internal assisted pumping of blood.

Another embodiment refers to an inhibitor of FXII/FXIIa for use in the prevention of the formation and/or stabilization of thrombi during and/or after a medical procedure performed on a human or animal subject comprising contacting blood of said human or animal subject with artificial surfaces, wherein said inhibitor of FXII/FXIIa is administered before, during and/or after said medical procedure, and wherein said human or animal subject has not an increased bleeding risk or wherein said human or animal subject has a reduced bleeding risk compared to the bleeding risk associated with the administration of heparin or derivatives thereof and/or hirudin or derivatives thereof. Preferably the bleeding risk is not increased.

Another embodiment refers to an inhibitor of FXII/FXIIa for use in the prevention of the formation and/or stabilization of thrombi during and/or after a medical procedure performed on a human or animal subject comprising contacting blood of said human or animal subject with artificial surfaces, wherein said inhibitor of FXII/FXIIa is administered before, during and/or after said medical procedure, and wherein said human or animal subject has not an increased bleeding risk and wherein in said human or animal subject i) the ear or finger tip bleeding time according to Duke is not longer than 10 minutes or ii) the bleeding time according to the method of Ivy is no longer than 10 minutes or iii) the bleeding time according to the method of Marx is no longer than 4 minutes.

In certain embodiments, the medical procedure is
 i) any procedure requiring a cardiopulmonary bypass or
 ii) the oxygenation and pumping of blood via extracorporeal membrane oxygenation or
 iii) the assisted pumping of blood (internal or external) or
 iv) the dialysis of blood or
 v) the extracorporeal filtration of blood or
 vi) the collection of blood in any repository for later use in an animal or a human subject or
 vii) the use of venous or arterial intraluminal catheter(s) or
 viii) the use of device(s) for diagnostic or interventional cardiac catherisation or
 ix) the use of intravascular device(s) or
 x) the use of artificial heart valve(s) or
 xi) the use of artificial grafts.

In another embodiment, a medical device is provided, wherein the medical device is coated with an inhibitor of FXII/FXIIa. The medical device may be a cardiopulmonary bypass machine, an extracorporeal membrane oxygenation system for oxygenation of blood, a device for assisted pumping of blood, a blood dialysis device, a device for the extracorporeal filtration of blood, a repository for use in the collection of blood, an intraluminal catheter, a stent, an artificial heart valve and/or accessories for any of these devices including tubing, cannulae, centrifugal pump, valves, ports, diverters, etc.

In one embodiment, the inhibitor of FXII/FXIIa is administered before, after and/or during a medical procedure comprising the collection of blood in any repository for later use in an animal or human subject. In one embodiment, the FXII/FXIIa inhibitor is administered to the blood donor before and/or during the blood donation process.

In another embodiment, the FXII/FXIIa inhibitor is mixed with the blood in the collection repository. In yet another embodiment, the FXII/FXIIa inhibitor is located in the collection repository before the collection of blood, and may be coated on the interior surface of the repository. In another embodiment, the FXII/FXIIa inhibitor is administered to the blood recipient before, during, and/or after the blood is administered to the human or animal recipient.

In other embodiments, the inhibitor of FXII/FXIIa is administered with heparin or derivatives thereof and/or hirudin or derivatives thereof wherein a reduced amount of heparin or derivatives thereof and/or hirudin or derivatives thereof is added in addition to the FXII/FXIIa inhibitor before and/or during and/or after the medical procedure as compared to the amount of heparin or derivatives thereof and/or hirudin or derivatives thereof which is administered normally before and/or during said medical procedure when no inhibitor of FXII/FXIIa is administered. By administered with, it is meant administered at the same time (in either a single formulation or two separate formulations), or administered within 1 minute, 5, 10, 15, 30, or 45 minutes, or 1 hour, 2, 3, 4, 5, or 6 hours, or administered at different times but for the same medical procedures. Either agent may be administered first.

Heparin derivatives consist of a group of products derived from heparin, made by one or more chemical modifications. For example, sulfated heparin is a derivative in which all primary hydroxyls in glucosamine residues and a large proportion of secondary hydroxyl groups in disaccharide units have been substituted by O-sulfate esters; carboxyl reduced heparin is a derivative in which the carboxyl group of uronic acid residues of heparin have been reduced to alcohols; periodate-oxidized heparin is a derivative in which all unsulfated uronic acid residues of heparin are oxidized by periodic acid. Other heparin derivatives include, for example, de-O-sulfated heparin, 2-O-desulfated heparin, fully N-acetylated heparin, fully N-sulfated heparin, de-N-sulfated heparin, de-N-acetylated heparin. Hirudin derivatives may also contain chemical modifications, which are to the hirudin peptide, or derivatives may be synthetic analogues of the hirudin peptide, and/or may comprise the hirudin peptide linked to, for example, a carrier molecule, which may be used, for example, to increase the half-life of hirudin. Examples of hirudin derivatives include, lepirudin, and desirudin. Hirudin derivatives are characterized in that they bind the active catalytic site of thrombin.

In one embodiment, heparin or derivatives thereof and/or hirudin or derivatives thereof which are administered with the FXII/FXIIa inhibitor are administered in a reduced amount such that the ACT without the FXII/FXIIa inhibitor is below 500 seconds.

In another embodiment, the inhibitor of FXII/FXIIa is administered in a medical procedure without the administration of heparin or a derivative thereof and/or the administration of hirudin or a derivative thereof.

In one embodiment the human or animal subject has a reduced a no prothrombotic risk after the medical procedure. In another embodiment, the human or animal subject has a reduced or no prothrombotic risk following the postoperative antagonism of heparin or derivatives thereof and/or the postoperative antagonism of hirudin or derivatives thereof is prevented or reduced by using a FXII/FXIIa inhibitor.

In another embodiment, the prothrombotic risk following the postoperative antagonism of heparin or derivatives thereof and/or the postoperative antagonism of hirudin or derivatives thereof is prevented or reduced by administering the inhibitor of FXII/FXIIa before, during and/or after a medical procedure, wherein a reduced or no amount of heparin antagonist and/or hirudin antagonist is added after the medical procedure compared to the amount of said antagonist which is administered normally after said medical procedure when no inhibitor of FXII/FXIIa is administered.

In one embodiment, the inhibitor of FXII/FXIIa, which is used according to the current invention, comprises
(i) the wild type Infestin-4 polypeptide sequence (SEQ ID NO: 1), or a variant thereof, wherein a variant comprises
 (a) the N-terminal amino acids 2-13 of the wild type Infestin-4 sequence and at least one and up to five amino acid mutations outside said N-terminal amino acids that result in differences from the wild type Infestin-4 sequence; and/or
 (b) six conserved cysteine residues from the wild type Infestin-4 sequence and a homology of at least 70% to the wild type Infestin-4 sequence.
(ii) SPINK-1 (SEQ ID NO:2), which is mutated to include the N-terminal amino acids 2-13 of the wild type Infestin-4 sequence, or a variant of said mutated SPINK-1, wherein a variant comprises
 (a) the N-terminal amino acids 2-13 of the wild type Infestin-4 sequence; and at least one and up to five amino acid mutations outside said N-terminal amino acids that result in differences from the wild type SPINK-1 sequence and which increase the homology of the variant to the wild type Infestin-4 sequence; and/or
 (b) six conserved cysteine residues from the wild type SPINK-1 sequence and a homology of at least 70% to the wild type SPINK-1 sequence.
(iii) AT III, angiotensin converting enzyme inhibitor, C1 inhibitor, aprotinin, alpha-1 protease inhibitor, antipain ([(S)-1Carboxy-2-Phenylethyl]-Carbamoyl-L-Arg-L-Val-Arginal), Z-Pro-Pro-aldehyde-dimethyl acetate, DX88, leupeptin, inhibitors of prolyl oligopeptidase such as Fmoc-Ala-Pyr-CN, corn-trypsin inhibitor (CTI), mutants of the bovine pancreatic trypsin inhibitor, ecotin, YAP (yellowfin sole anticoagulant protein) and *Cucurbita maxima* trypsin inhibitor-V, Curcurbita maxima isoinhibitors, and Pro-Phe-Arg-chloromethyl-ketone (PCK);
(iv) an anti-FXII/FXIIa antibody, wherein the antibody binds to FXII/FXIIa and inhibits its activity and/or activation.

In one embodiment, the inhibitor of FXII/FXIIa, which is used according to the current invention, is linked to a half-life enhancing polypeptide, wherein the half-life enhancing peptide is optionally albumin, afamin, alpha-fetoprotein or vitamin D binding protein, human albumin, or a variant thereof, an immunoglobulin or variant thereof, an Fc of an IgG. In another embodiment said half-life enhancing polypeptide is linked to the FXII/FXIIa inhibitor via a linker.

DESCRIPTION OF THE DRAWINGS

FIG. 1: Ex vivo whole blood clotting time (WBCT) of porcine whole blood can be dramatically prolonged following spiking with the FXII/FXIIa inhibitor rHA-Infestin-4. Required volume of rHA-Infestin-4 was provided in a syringe. Then porcine whole blood was added to a total volume of 500 µL, gently mixed and thereafter given in a pre-warmed glass vial. Clotting time was determined visually by gently shaking the glass vial every minute (incubation at 37° C. in a water bath). Data are presented as mean+standard error of the mean. N=whole blood of 2-3 pigs at each concentration.

FIG. 2: Ex vivo WBCT of murine whole blood can be prolonged following spiking with an anti-FXII/FXIIa monoclonal antibody (MAb). The required volume of an anti-FXII/FXIIa MAb was provided in a syringe. Then murine whole blood was added to a total volume of 500 µL, gently mixed and thereafter given in a pre-warmed glass vial. Clotting time was determined visually by gently shaking the glass vial every minute (incubation at 37° C. in a water bath). Data are presented as mean+standard error of the mean. N=whole blood of 3 mice at each concentration.

FIG. 3: Ex vivo WBCT of porcine whole blood is markedly prolonged following a single intravenous (i.v.) administration of rHA-Infestin-4. At specific time points following administration, blood was taken from the animals and given in a pre-warmed glass vial. Clotting time was determined visually by gently shaking the respective glass vial every minute (incubation at 37° C. in a water bath).

FIG. 4: The aPTT of porcine blood was markedly prolonged after the administration of rHA-Infestin-4 compared to the negative control.

FIG. 5: The PT of porcine blood was only marginally prolonged after the administration of higher doses of rHA-Infestin-4 as compared to the prolongation of the aPTT.

FIG. 6: The porcine skin bleeding time remained in the normal range (~2-5 min.) after rHA-Infestin-4 was administered. This effect lasted until the end of the experiment.

FIG. 7: The extracorporeal circulation in the porcine model was performed according to the graph displayed in FIG. 7.

FIG. 8: After rHA-Infestin-4 administration, the aPTT of the porcine blood remained markedly prolonged during the whole experiment on extracorporeal circulation.

FIG. 9: The PT of the porcine blood was only slightly influenced after the administration of rHA-Infestin-4 during the extracorporeal experiment.

FIG. 10: Ex vivo WBCT of porcine whole blood is prolonged throughout the whole extracorporeal experiment following a single i.v. administration of rHA-Infestin-4. At specific time points, blood was taken from this animal and given in a pre-warmed glass vial. Clotting time was determined visually by gently shaking the glass vial every minute (incubation at 37° C. in a water bath).

FIG. 12: Amino acid sequence similarity between Infestin-4 (I4) and SPINK-1 (SP). * denotes identical amino acid; | denotes similar amino acid; bold amino acids are conserved cysteines; underlined amino acids 2-13 of the Infestin-4 sequence are conserved.

FIG. 13: Amino acid sequences of Infestin-4, SPINK1 and three SPINK1 variants (K1, K2, and K3). * denotes identical; | similar amino acids with regard to the Infestin-4 sequence. The underlined sequence of I4 was used to replace 15 amino acids of SPINK-1 to generate K1. Variants K2 and K3 were generated by additional point mutations (amino acids underlined) on the K1 sequence.

DETAILED DESCRIPTION

Figure 11:
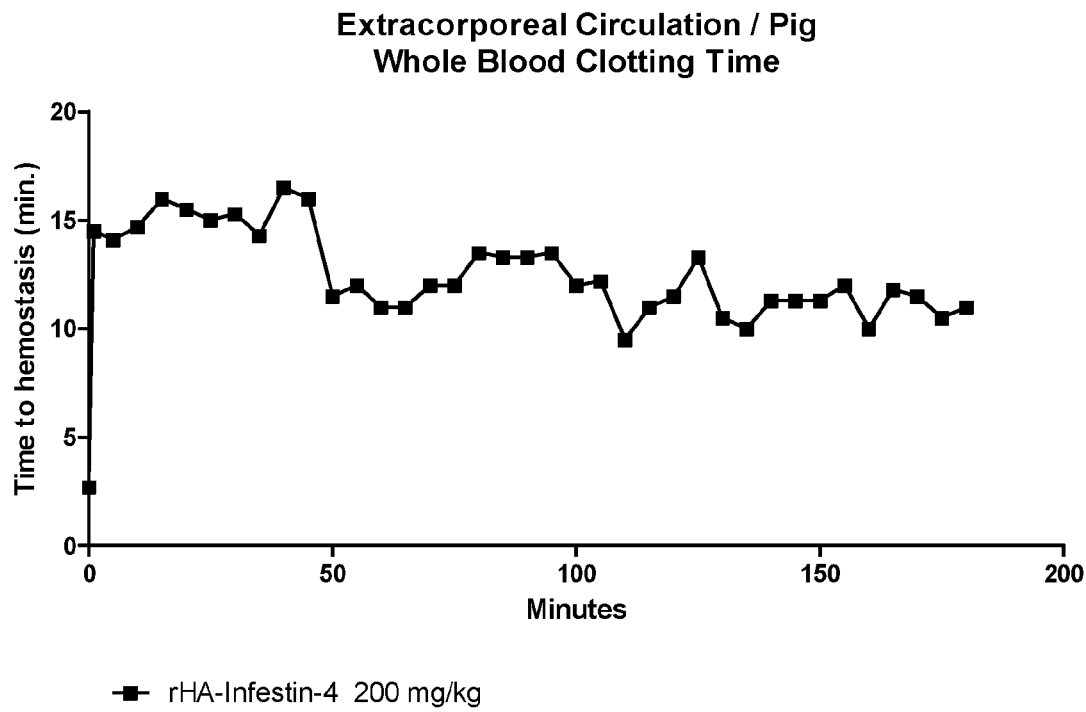
FIG. 11: Contact sites of *R. prolixus* inhibitor with thrombin and of SPINK-1 with chymotrypsin. # denotes amino acids that are contact sites between *R. prolixus* inhibitor and thrombin; + denotes amino acids that are contact sites between SPINK-1 and chymotrypsin.

A FXII/FXIIa inhibitor refers to inhibitors of either or both of Factor XII and activated Factor XII (FXIIa).

The application provides an inhibitor of FXII/FXIIa for use in the prevention of the formation and/or stabilization of thrombi during and/or after a medical procedure performed on a human or animal subject comprising contacting blood of said human or animal subject with artificial surfaces, wherein said inhibitor of FXII/FXIIa is administered before, during and/or after said medical procedure.

An artificial surface is any non human or non animal surface which is contacted with blood during a medical procedure and which leads to the contact activation of Factor XII to Factor XIIa. In certain embodiments, contact between a subject's blood and the artificial surface occurs outside of the subject's body. By way of non-limiting example such artificial surfaces may be steel, any type of plastics, glass, silicon, rubber, etc. In one embodiment, the artificial surface is exposed to at least 80%, 90%, or 100% of the blood of the human or animal subject. In another embodiment, the volume of 80%, 90%, or 100% of the blood of the human or animal subject contacts the artificial surface in less than 30 minutes, less than 15 minutes, less than 10 minutes, or less than 5 minutes. In another embodiment, the artificial surface serves as a container for blood outside of the human or animal body, and such blood may be in the amount of at least 50 mL, 100 mL, 200 mL, 300 mL, 400 mL, 500 mL or more. In one embodiment, the artificial surface being exposed to the patient's blood is at least 0.2 m². In one embodiment, the entire volume of the patient's blood is exposed to the artificial surface, which is at least 0.2 m². In embodiments, the artificial surface area is at least 0.1 m², or at least 0.5 m². In another embodiment, the artificial surface excludes retractors, needles, scalpels and other routine surgical equipment that only come in contact with a fraction of a subject's blood.

In one embodiment, the FXII/FXIIa inhibitor is administered before, during, and/or after the medical procedure. In another embodiment, the FXII/FXIIa inhibitor is administered during the medical procedure. In another embodiment, it may also be administered before the medical procedure is started. It may even be beneficial to be administered after the medical procedure since a contact activation may occur on artificial surfaces that had been integrated in vessels during operations.

Another embodiment refers to an inhibitor of FXII/FXIIa for the prevention of the formation and/or stabilization of thrombi during and/or after a medical procedure performed on a human or animal subject comprising contacting blood of said human or animal subject with artificial surfaces, wherein contact between the blood and the artificial surface occurs outside the subject's body, wherein said inhibitor of FXII/FXIIa is administered before, during and/or after said medical procedure, and wherein said human or animal subject has not an increased bleeding risk. In embodiments, contact between said subject's blood and at least a portion of the artificial surface occurs "outside" of a subject's body, which in certain embodiments is at least 1 cm, or 2 cm, or 3 cm, or 4 cm, or 5 cm, or 10 cm, or 15 cm, or 20 cm, or 50 cm, or more away from the subject's body.

Another embodiment refers to an inhibitor of FXII/FXIIa for the prevention of the formation and/or stabilization of thrombi during and/or after a medical procedure performed on a human or animal subject comprising contacting blood of said human or animal subject with artificial surfaces, wherein said inhibitor of FXII/FXIIa is administered before, during and/or after said medical procedure, and wherein said human or animal subject has not an increased bleeding risk and wherein in said human or animal subject i) the ear or finger tip bleeding time according to Duke is not longer than 10 minutes, not longer than 8 minutes, not longer than 6 minutes or not longer than 5 minutes or ii) the bleeding time according to the method of Ivy is not longer than 10 minutes, not longer than 8 minutes, not longer than 6 minutes or not longer than 5 minutes or iii) the bleeding time according to the method of Marx is not longer than 4 minutes, not longer than 3 minutes or not longer than 2 minutes. In other words: due to the administration of a FXII/FXIIa inhibitor The determination of the bleeding risk according to Duke, Ivy or Marx are only non-limiting examples of methods which can be used to determine the bleeding risk in human or animal subjects. In animals the bleeding risk may also be assessed by determining the skin bleeding time. For example in pigs, the skin bleeding time (SBT) can be defined as the time until cessation of blood loss from a standardized 5 mm long by 1 mm deep inner ear incision created by using a Surgicute cutting device (International Technidyne Corp., Edison, N.J., USA).

In comparison to this animal test above-mentioned test methods for humans are described below.

The bleeding time according to the Duke method is performed on the rim of the earlobe, or the finger tip with blood pressure cuff around the upper arm (40 mm Hg), of a subject. The investigator punctures the rim of the earlobe, or the finger tip, with a lancet and induces a tissue damage which is ~3 mm deep. Then the investigator let the blood drop out of the tissue damage via gravity without compromising the damage technically, or manually. The dripping blood is wiped away with a cellulose paper every 15 to 30 sec without touching the lesion. This procedure is repeated until a cessation is detected by the investigator via visual inspection. Normal values for this visual assessed bleeding test are up to 5 minutes. However there are certain variations depending also on the individual subject, so that the normal bleeding time according to Duke can also be up to 6 minutes, or up to 8 minutes or up to 10 minutes.

The bleeding time according to the Ivy method is performed with a defined cut in the skin of the inner side of the forearm (e.g. Surgicutt®), while a standardized tissue pressure is created via a blood pressure cuff (40 mm Hg) on the upper arm of the subject. The investigator wipes away the blood that runs out of the lesion via gravity every 30 sec without touching the lesion. Then the time is taken until bleeding stops. Normal values for this visual assessed bleeding test are up to 5 minutes. However there are certain variations depending also on the individual subject, so that the normal bleeding time according to Ivy can also be up to 6 minutes, or up to 8 minutes or up to 10 minutes.

The subaquale bleeding time according to Marx is performed via tissue damage created on the finger tip of a subject by using a lancet. After the tissue damage is made, the finger tip needs to be inserted into water at 37° C. immediately. Then, while the finger remains underwater, the investigator visually inspects the bleeding and monitors the time until the bleeding stops without compromising the tissue damage. Normal values for this visual assessed bleeding test are up to 2 minutes. However there are certain variations depending also on the individual subject, so that the normal bleeding time according to Marx can also be up to 3 minutes or up to 4 minutes.

In certain embodiments, the medical procedure is by way of non-limiting examples:

i) any procedure using cardiopulmonary bypass (CBP), including for example, coronary artery bypass graft (CABG), valve replacement, aortic replacement, and other forms of cardiac or vascular surgery; or ii) the oxygenation and pumping of blood via extracorporeal membrane oxygenation (ECMO), which is used for patients with acute respiratory distress syndrome (ARDS), or for infant respiratory distress syndrome (IRDS), or for patients, who aspirated toxic substances, or for the meconium aspiration syndrome (MAS), or lung infections, or pulmonal hypertension, or heart failure for various reasons as for example post cardiac surgery, as a result of cardiomyopathy or prior to heart transplantation; or iii) the assisted pumping of blood (internal or external) including artificial hearts and ventricular assist devices; or iv) the dialysis of blood; or v) the extracorporeal filtration of blood; or vi) the collection of blood in any repository for later use in an animal or a human subject; or vii) the use of venous or arterial intraluminal catheter(s) which are supposed to stay for a certain time (e.g. Swan-Ganz catheter, central venous catheter, etc.); or viii) the use of catheters, sheaths, guidewires or other equipment/device(s) for diagnostic or interventional cardiac catheterisation; or ix) the use of intravascular device(s) such as stent(s), vena cava filter(s), Atrial Septal Defect (ASD), Ventricular Septal Defect (VSD) or Persistent Ductus Arteriosus (PDA) occluder(s), coil(s); or x) the use of artificial heart valve(s) including for example aortic valves, mitral valves, tri-cuspid valves, pulmonary valves, and whereby a heart valve may be a mechanical valve, or a bioprosthetic valve, a tissue engineered valve, or a stent mounted valve; or xi) the use of artificial vascular graft(s), including for example, Gore-tex aortic graft(s), pulmonary graft(s), and modified Blalock-Taussig (BT) shunt(s).

In general, there are several medical scenarios in which blood gets into contact with artificial surfaces inside and outside of the human body, which can then result in clot formation as a consequence of coagulation activation on these surfaces.

External contact (outside of the human body) can be summarized as procedures including an extracorporeal circulation so that blood is taken out of the body and after a while returned into the body (bypass, ECMO, hemofiltration, dialysis, collection of blood etc).

Internal contact (inside of the human body) to foreign surfaces is given in all procedure using intravascular devices, both those permanently implanted (heart valves stents, etc) and those only temporarily employed (catheters, guide wires etc.).

In another embodiment, a medical device is provided, wherein the medical device is coated with an inhibitor of FXII/FXIIa. The medical device may be a cardiopulmonary bypass machine, an extracorporeal membrane oxygenation system for oxygenation of blood, an device for assisted pumping of blood, a blood dialysis device, a device for the extracorporeal filtration of blood, a repository for use in the collection of blood, an intraluminal catheter, a stent, an artificial heart valve and/or accessories for any of these devices including tubing, cannulae, centrifugal pump, valves, ports, diverters, etc. Another embodiment includes methods of preparing such devices by coating them with FXII/FXIIa inhibitors by dipping, spraying, and other methods conventional in the art of coating technologies.

In embodiments, the FXII/FXIIa inhibitor is coated onto the artificial surface, wherein the FXII/FXIIa inhibitor is on the surface in a way such that it is available for binding to FXII/FXIIa, i.e. the biological activity of the FXII/FXIIa inhibitor is preserved. In embodiments, the FXII/FXIIa inhibitor is covalently attached to the artificial surface. In other embodiments, the FXII/FXIIa inhibitor is non-covalently attached to the surface. In certain embodiments, the artificial surface is impregnated with the FXII/FXIIa inhibitor. The artificial surface may be a drug-eluting surface, wherein the FXII/FXIIa inhibitor is slowly released from the surface. The FXII/FXIIa inhibitor may be embedded in the surface, wherein the FXII/FXIIa inhibitor slowly dissolves as blood contacts the artificial surface. In embodiments, the surface is derivatized for FXII/FXIIa inhibitors to adhere to the surface. In certain embodiments the concentration of FXII/FXIIa inhibitor that is coated on the surface may be similar to the amount administered to a subject systemically. Concentrations of FXII/FXIIa inhibitor solutions and/or the final concentration of FXII/FXIIa inhibitor available on the artificial surface may be determined before and/or during manufacturing. In embodiments, the FXII/FXIIa inhibitor is administered by being coated on the artificial surface of the device.

In other embodiments, the inhibitor of FXII/FXIIa is administered with heparin or derivatives thereof and/or hirudin or derivatives thereof wherein the amount of heparin or derivatives thereof and/or hirudin or derivatives thereof which is added in addition to the FXII/FXIIa inhibitor before and/or during and/or after the medical procedure is reduced as compared to the amount of heparin or derivatives thereof and/or hirudin or derivatives thereof which is administered normally before and/or during said medical procedure when no inhibitor of FXII/FXIIa is administered.

Standard therapy in the above mentioned medical procedures is the administration of heparin or derivatives thereof and/or hirudin or derivatives thereof. These drugs are administered to prevent clotting due to the contact activation taking place where blood comes into contact with artificial surfaces. To achieve a prevention of clotting these drugs are dosed such that the Activated Clotting Time (ACT) is between 300-500 seconds. At ACT values below 300 seconds performing the above mentioned medical procedures would entail a high risk of thrombosis.

Administration of FXII/FXIIa inhibitors was found to enable performing the above mentioned medical procedures with reduced amounts of heparin or derivatives thereof and/or hirudin or derivatives thereof which would on their own without the administration of a FXII/FXIIa inhibitor lead to ACT values below 500 seconds.

Embodiments include performing the above mentioned medical procedures with further reduced amounts of heparin or derivatives thereof and/or hirudin or derivatives thereof such that the ACT values would be below 400 seconds, below 300 seconds, below 250 seconds, below 200 seconds, below 150 seconds, below 100 seconds, below 50 seconds when the heparin or derivatives thereof and/or hirudin or derivatives thereof would be given on their own without the administration of a FXII/FXIIa inhibitor. Such reduced amounts of heparin may include from 1 to 400 IU/kg body weight (BW), 50 to 300 IU/kg BW, 100 to 200 IU/kg BW, and 200 to 300 IU/kg BW). Reduced amount of heparin may include amounts below 400 IU/kg body weight (BW), amounts below 300 IU/kg body weight (BW), amounts below 200 IU/kg body weight (BW), amounts below 100 IU/kg body weight (BW), amounts below 50 IU/kg body weight (BW), or amounts below 10 IU/kg body weight (BW).

In one embodiment the inhibitor of FXII/FXIIa is administered in a medical procedure as described above without the administration of heparin or a derivative thereof and/or without the administration of hirudin or a derivative thereof.

Patients treated in the above mentioned medical procedures without the administration of heparin or a derivative thereof and/or without the administration of hirudin or a derivative thereof in addition to the administration of a FXII/FXIIa inhibitor are protected against clotting due to contact activation of the coagulation cascade while not suffering from an increased bleeding risk which is a drawback of the current standard therapy. This is of major importance for patients and physicians since the coagulation status after the mentioned medical procedures is not adequately reflected by the general coagulations test (e.g. aPTT, PT) and therefore cannot monitored and treated adequately. The patient itself may show signs of hypercoagulopathy or hypocoagulopathy. In some countries, patients are therefore not anticoagulated in a timely manner after the medical procedure just because of potential medical legal reasons in case of severe bleeding after surgery, while the risk of clotting is related to the personal patient's risks.

Due to this increased bleeding risk associated with the administration of heparin or a derivative thereof after the medical procedure is performed and the blood of the human or animal subject is no longer exposed to artificial surfaces, the effect of heparin or a derivative thereof must be antagonized as early as possible to reduce the increased bleeding risk as early as possible. To antagonize the effect of heparin or derivatives thereof, usually protamine is given; however, antagonism presents its own risks as described below. In case hirudin or a derivative thereof is used instead or in combination with heparin or a derivative thereof, it would also be beneficial to antagonize the effects of hirudin or a derivative thereof as the bleeding risk is also increased, although a clinically-useful antagonist has not yet been licensed and therefore remaining unantagonized hirudin or a derivative thereof presents risks. Should such antagonists of hirudin or derivatives thereof become available it is foreseeable that the use of the antagonists would carry a prothrombotic risk comparable to that of the use of heparin antagonists.

The risks associated with the administration of protamine are, an immediate severe allergic reaction caused by protamine molecule, the risk for severe hypotension and the risk for clotting due to the sudden cessation of the heparin effect, which may cause overshooting thrombin generation.

Therefore in another embodiment, the prothrombotic risk following the postoperative antagonism of heparin or derivatives thereof and/or the postoperative antagonism of hirudin or derivatives thereof is prevented or reduced by using a FXII/FXIIa inhibitor.

In another embodiment, the prothrombotic risk following the postoperative antagonism of heparin or derivatives thereof and/or the postoperative antagonism of hirudin or derivatives thereof is prevented or reduced by administering the inhibitor of FXII/FXIIa before, during and/or after a medical procedure, wherein a reduced or no amount of heparin antagonist and/or hirudin antagonist is added after the medical procedure compared to the amount of said antagonist which is administered normally after said medical procedure when no inhibitor of FXII/FXIIa is administered.

In a more general way, in one embodiment, the human or animal subject has a reduced a no prothrombotic risk after the medical procedure.

As discussed above, "FXII/FXIIa" refers to either or both of Factor XII and activated Factor XII (FXIIa). Thus "FXII/FXIIa inhibitor" includes inhibitors of either or both of FXII and FXIIa. Further, anti-FXII/FXIIa antibodies include antibodies that bind to and inhibit either or both of FXII and FXIIa. The term "FXII/FXIIa inhibitor" is also meant to include an inhibitor of FXII/FXIIa that is linked to a half-life extending polypeptide, which in one embodiment, includes a linker.

In one embodiment the FXII/FXIIa inhibitor is a specific FXII/FXIIa inhibitor, preferably a specific FXIIa inhibitor.

A specific FXII/FXIIa inhibitor refers to an inhibitor which inhibits plasmatic serine proteases other than FXII and/or FXIIa less than or equal to 25% if used in a molar ratio of 1:1. In other words: a specific FXII/FXIIa inhibitor inhibits plasmatic serine proteases other than FXII and/or FXIIa less than or equal to 25% when said inhibitor is used in a molar ratio of 1:1 of the respective plasmatic serine protease to said inhibitor. For example, a specific FXII/FXIIa mAb inhibits the plasmatic serine protease FXIa by only 5%, wherein the molar ratio of FXIa to said mAb is 1:1 whereas the same FXII/FXIIa mAb inhibits FXIIa by at least 80%, preferably at least 90%.

In one embodiment of the invention one other plasmatic serine protease is inhibited by more than 50% if used in a molar ratio of 1:1 of the respective plasmatic serine protease to said inhibitor.

In another embodiment of the invention two other plasmatic serine proteases are inhibited by more than 50% if used in a molar ratio of 1:1 of the respective plasmatic serine protease to said inhibitor.

In yet another embodiment the FXII/FXIIa inhibitor is a human FXII/FXIIa inhibitor, including a humanized monoclonal antibody, preferably a fully humanized monoclonal antibody.

"Homology" as used herein refers to the percentage number of amino acids that are identical or constitute conservative substitutions. Homology may be determined using sequence comparison programs such as GAP (Deveraux et al., 1984, Nucleic Acids Research 12, 387-395), which is incorporated herein by reference. In this way sequences of a similar or substantially different length to those cited herein could be compared by insertion of gaps into the alignment, such gaps being determined, for example, by the comparison algorithm used by GAP.

Infestin-4

In one embodiment, the application provides a FXII/FXIIa inhibitor comprising Infestin domain 4, Infestin-4. In one embodiment, a FXII/FXIIa inhibitor comprises a variant of Infestin-4. In another embodiment, FXII/FXIIa inhibitors comprise Infestin domain 4, and optionally Infestin domains 1, 2, and/or 3; these proteins are known to be potent inhibitors of FXII/FXIIa (see WO 2008/098720; also see Campos ITN et al. 577 *FEBS Lett.* 512-516, 2004). The wild type polypeptide sequence of Infestin-4 is provided (SEQ ID NO: 1). As used herein, the term "variant" refers to a polypeptide with an amino acid mutation, wherein a "mutation" is defined as a substitution, a deletion, or an addition, to the wild type Infestin-4 sequence, wherein such changes do not alter the functional ability of the polypeptide to inhibit FXII/FXIIa. The term "variant" includes fragments of the wild type or mutated Infestin-4 sequence. Further examples of such variants are provided below.

In one embodiment, an Infestin-4 variant comprises the N-terminal amino acids 2-13 of the wild type Infestin-4 sequence (see underlined sequence in FIG. 12), and at least one and up to five amino acid mutations outside the N-terminal amino acids that result in differences from the wild type Infestin-4 sequence, or six conserved cysteine residues (see amino acids in bold in FIG. 12) and homology of at least 70% to the wild type Infestin-4 sequence. The N-terminal amino acids 2-13 of the Infestin-4 sequence may be important for binding to FXII/FXIIa based on analysis of structural data for a related inhibitor *Rhodnius prolixus* (PDB: 1 TSO) binding to thrombin, and analysis of SPINK-1 binding to chymotrypsin, which both share a common feature of the accumulation of contact sites in the N-terminal region as shown in FIG. 11. Therefore in one embodiment, a variant of Infestin-4 comprises the conserved N-terminal region of amino acids 2-13 of the wild type Infestin-4 sequence, and at least one and up to five amino acid mutations outside these conserved N-terminal amino acids that result in differences from the wild type Infestin-4 sequence. A mutation may be a substitution, a deletion, or an addition. As used herein, the term "outside said N-terminal amino acids" refers to any amino acid along the polypeptide chain of the variant other than the contiguous stretch of amino acids that comprises the sequence VRNPCACFRNYV, i.e., amino acids 2-13 from the wild type Infestin-4 sequence. In another embodiment, an Infestin-4 variant comprises six conserved cysteine residues and has homology of at least 70% to the wild type Infestin-4 sequence. In one embodiment, the six conserved cysteine residues are amino acids at positions 6, 8, 16, 27, 31, and 48 of the wild type Infestin-4 sequence (see FIG. 12). In one embodiment, the variant comprises the final conserved cysteine. In other embodiments, the exact positions of the cysteine residues, and relative positions to each other, may change from positions 6, 8, 16, 27, 31, and 48 of the wild type Infestin-4 sequence due to insertions or deletions in the Infestin-4 variant. Nevertheless, in these embodiments, an Infestin-4 variant comprises all six cysteines and may share 70%, 75%, 85%, 90%, 91%, 92%, 93%, 94%, 95%, 96%, 97%, 98% or 99% homology to the wild type Infestin-4 sequence.

In embodiments, a variant of Infestin-4 is characterized in that it inhibits FXII/FXIIa. The functional activity of inhibiting FXII/FXIIa may be assessed for example, through in vitro and/or in vivo characterization, including direct assays to test inhibition of FXII/FXIIa enzyme activity, prolonged coagulation time, i.e. activated partial thromboplastin time (aPTT), or in vivo methods that evaluate coagulation. Further examples of Infestin-4 variants are SPINK-1 mutants, which are described below.

SPINK-1 Mutants

One embodiment involves FXII/FXIIa inhibitors for therapeutic use in humans. A human protein with high similarity to Infestin-4 may be employed. For example, the human protein with the highest similarity to Infestin-4 is SPINK-1, a Kazal-type serine protease inhibitor expressed in the pancreas (also known as pancreatic secretory trypsin inhibitor, PSTI). The Kazal-type serine protease inhibitor family is one of numerous families of serine protease inhibitors. Many proteins from different species have been described (Laskowski M and Kato I, 49 *Ann. Rev. Biochem.* 593-626, 1980). The amino acid sequence similarities between Infestin-4 and SPINK-1 are outlined in FIG. 12.

Based on the wild type SPINK-1 sequence (SEQ ID NO: 2) different variants may be generated in order to increase homology of the SPINK-1 sequence to Infestin-4. The phrase "increased homology to Infestin-4" refers to the process whereby amino acid mutations are made to SPINK-1 to bring the SPINK-1 sequence closer to the Infestin-4 sequence.

In one embodiment, SPINK-1 is mutated to comprise the N-terminal amino acids 2-13 of the wild type Infestin-4 sequence; the polypeptide sequence is given and is referred to as K1 (SEQ ID NO: 3). As described above, the N-terminal portion of the Infestin-4 sequence is thought to be important for FXII/FXIIa inhibitory function.

Therefore, in one embodiment, a variant of the mutated SPINK-1 also comprises N-terminal amino acids 2-13 of the wild type Infestin-4 sequence, and at least one and up to five amino acid mutations outside said N-terminal amino acids that result in differences from the wild type SPINK-1 sequence and which increase the homology of the variant to the wild type Infestin-4 sequence. In another embodiment, a variant of mutated SPINK-1 comprises six conserved cysteine residues and has homology of at least 70% to the wild type SPINK-1 sequence. A mutation may be a substitution, a deletion, or an addition. As defined above, the term "outside said N-terminal amino acids" refers to any amino acid along the polypeptide chain of the variant other than the contiguous stretch of amino acids that is comprised of the sequence VRNPCACFRNYV, i.e., amino acids 2-13 from the wild type Infestin-4 sequence. The term "variant" includes fragments of said mutated SPINK-1 sequence. In one embodiment, the six conserved cysteine residues may be amino acids at positions 9, 16, 24, 35, 38, and 56 of the wild type SPINK-1 sequence (see FIG. 12). In one embodiment, the variant comprises the final conserved cysteine. In another embodiment, the exact positions of the cysteines, and relative positions to each other, may change from positions 9, 16, 24, 35, 38, and 56 of the wild type SPINK-1 sequence due to insertions or deletions in the SPINK-1 variant. Nevertheless, in these embodiments, a SPINK-1 variant comprises all six cysteines. In embodiments, a SPINK-1 variant is also characterized in that it inhibits FXII/FXIIa.

Examples of such SPINK-1 variants are given and are named K2, and K3 (SEQ ID NO: 4 and 5 respectively). In SPINK-1 variants K2 and K3, further amino acid substitutions outside of the N-terminus were made in order to increase homology to Infestin-4, wherein the variants are also characterized in that they inhibit FXII/FXIIa activity. See WO 2008/098720. FIG. 13 shows the amino acid sequence of these variants and the degree of changes to the SPINK-1 wild-type sequence. In the case of the SPINK-1 variant K3, five amino acid substitutions were made to increase homology to Infestin-4. Thus in embodiments, a SPINK-1 variant may share 70%, 75%, 85%, 90%, 91%, 92%, 93%, 94%, 95%, 96%, 97%, 98% or 99% A homology with the wildtype SPINK-1 sequence.

Other FXII/FXIIa Inhibitors

In one embodiment, other inhibitors of FXII/FXIIa are administered to a patient receiving a medical procedure. In WO 2006/066878 the use of antibodies against FXII/FXIIa or the use of inhibitors of FXII/FXIIa is proposed. Specifically, inhibitors to FXII/FXIIa include antithrombin III (AT III), angiotensin converting enzyme inhibitor, C1 inhibitor, aprotinin, alpha-1 protease inhibitor, antipain ([(S)-1-Carboxy-2-Phenylethyl]-Carbamoyl-L-Arg-L-Val-Arginal), Z-Pro-Proaldehyde-dimethyl acetate, DX88 (Dyax Inc., 300 Technology Square, Cambridge, Mass. 02139, USA; cited in: Williams A and Baird LG, 29 *Transfus Apheresis* Sci. 255-258, 2003), leupeptin, inhibitors of prolyl oligopeptidase such as Fmoc-Ala-Pyr-CN, corn-trypsin inhibitor (CTI), mutants of the bovine pancreatic trypsin inhibitor, ecotin, yellowfin sole anticoagulant protein (YAP), *Cucurbita maxima* trypsin inhibitor-V including Curcurbita maxima isoinhibitors and Hamadarin (as disclosed by Isawa H et al. 277 *J. Biol. Chem.* 27651-27658, 2002), and Pro-Phe-Arg-chloromethyl-ketone (PCK).

The FXII/FXIIa inhibitor may be for example an antibody, or fragment of the same or mimetic retaining the inhibitory activity, for example analogues of Kunitz Protease Inhibitor domain of amyloid precursor protein as disclosed in U.S. Pat. No. 6,613,890 in columns 4 through 8. Other suitable inhibitors may be Hamadarin as disclosed in Isawa H et al. 277 *J. Biol. Chem.* 27651-27658, 2002. A suitable Corn Trypsin Inhibitor and methods of its production are disclosed in Chen Z et al. 65 *Applied and Environmental Microbiology,* 1320-1324, 1999, and in Wen L et al. 18 *Plant Mol. Biol.* 813-814, 1992.

In another embodiment, the FXII/FXIIa inhibitor may be an anti-FXII/FXIIa antibody that binds to FXII/FXIIa and inhibits FXII/FXIIa activation and/or activity. Such an antibody has been described for example in WO 2006/066878, and in Rayon et al., 1 *Blood* 4134-43, 1995. As discussed above, an "anti-FXII/FXIIa antibody" includes antibodies that bind to and inhibit either or both of FXII and FXIIa. Anti-FXII/FXIIa antibodies are described in further detail below.

FXII/FXIIa Inhibitors Linked to Half-Life Enhancing Polypeptides

Another aspect of the application provides FXII/FXIIa inhibitors linked to a half-life enhancing polypeptide (HLEP). In one embodiment, FXII/FXIIa inhibitors are small proteins. Therefore a rapid renal clearance as published for other small proteins can be expected (Werle M and Bernkop-Schnurch A, 30 *Amino Acids* 351-367, 2006). One way to address a short plasma half-life of a polypeptidic compound is to inject it repeatedly or via continuous infusion. Another approach is to increase the intrinsic plasma half-life of the polypeptide itself. For example, in one embodiment, FXII/FXIIa inhibitors are linked to half-life extending proteins.

A "half-life enhancing polypeptide" increases the half-life of the FXII/FXIIa inhibitor in vivo in a patient or in an animal. For example, albumin and immunoglobulins and their fragments or derivatives have been described as half-life enhancing polypeptides (HLEPs). Ballance et al. (WO 2001/79271) described fusion polypeptides of a multitude of different therapeutic polypeptides which, when fused to human serum albumin, are predicted to have an increased functional half-life in vivo and extended shelf-life.

The terms "albumin" and "serum albumin" encompass human albumin (HA) and variants thereof, the full mature form of which is given (SEQ ID NO: 6), as well as albumin from other species and variants thereof. As used herein, "albumin" refers to an albumin polypeptide or amino acid sequence, or an albumin variant, having one or more functional activities (e.g. biological activities) of albumin. As used herein, albumin is capable of stabilizing or prolonging the therapeutic activity of a FXII/FXIIa inhibitor. The albumin may be derived from any vertebrate, especially any mammal, for example human, monkey, cow, sheep, or pig. Non-mammalian albumins include, but are not limited to, albumin from hen and salmon. The albumin portion of the albumin-linked polypeptide may be from a different animal than the therapeutic polypeptide portion. See WO 2008/098720 for examples of albumin fusion proteins.

In one embodiment, an albumin variant is at least 10, 20, 40, or at least 70 amino acids long or may include 15, 20, 25, 30, 50 or more contiguous amino acids from the HA sequence (SEQ ID NO 6) or may include part or all of specific domains of HA. An albumin variant may include an amino acid substitution, deletion, or addition, either conservative or non-conservative substitution, wherein such changes do not substantially alter the active site, or active domain, which confers the therapeutic activities of the half-life enhancing polypeptides. These variants may share 70%, 75%, 85%, 90%, 91%, 92%, 93%, 94%, 95%, 96%, 97%, 98% or 99% homology.

In one embodiment, the albumin variant includes fragments and may consist of or alternatively comprise at least one whole domain of albumin or fragments of said domains, for example domains 1 (amino acids 1-194 of SEQ ID NO 6), 2 (amino acids 195-387 of SEQ ID NO 6), 3 (amino acids 388-585 of SEQ ID NO 6), 1+2 (1-387 of SEQ ID NO 6), 2+3 (195-585 of SEQ ID NO 6) or 1+3 (amino acids 1-194 of SEQ ID NO 6+amino acids 388-585 of SEQ ID NO 6). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

In another embodiment, other proteins that are structurally or evolutionarily related to albumin may be used as HLEPs, including, but not limited to alpha-fetoprotein (WO 2005/024044; Beattie and Dugaiczyk, 20 *Gene* 415-422, 1982), afamin (Lichenstein et al. 269 *J. Biol. Chem.* 18149-18154, 1994), and vitamin D binding protein (Cooke and David, 76 *J. Clin. Invest.* 2420-2424, 1985). Their genes represent a multigene cluster with structural and functional similarities mapping to the same chromosomal region in humans, mice, and rat. The structural similarity of the albumin family members suggest their usability as HLEPs. For example, alpha-fetoprotein, has been claimed to extend the half-life of an attached therapeutic polypeptide in vivo (WO 2005/024044). Such proteins, or variants thereof, that are capable of stabilizing or prolonging therapeutic activity may be used, and may be derived from any vertebrate, especially any mammal, for example human, monkey, cow, sheep, or pig, or non-mammal including but not limited to, hen or salmon. See WO 2008/098720. Such variants may be of 10 or more amino acids in length or may include about 15, 20, 25, 30, 50 or more contiguous amino acids of the respective protein sequence or may include part or all of specific domains of the respective proteins. Albumin family member fusion proteins may include naturally occurring polymorphic variants.

In another embodiment, an immunoglobulin (Ig), or variants thereof, may be used as an HELP, wherein a variant includes fragments. In one embodiment, the Fc domain or portions of the immunoglobulin constant region are used. The constant region may be that of an IgM, IgG, IgD, IgA, or IgE immunoglobulin. The therapeutic polypeptide portion is connected to the Ig via the hinge region of the antibody or a peptidic linker, which may be cleavable. Several patents and patent applications describe the fusion of therapeutic proteins to immunoglobulin constant regions to extend the therapeutic protein's half-life in vivo (US 2004/0087778, WO 2005/001025, WO 2005/063808, WO 2003/076567, WO 2005/000892, WO 2004/101740, U.S. Pat. No. 6,403,077). For example, an Fc fused to the cytokine IFN-β achieved enhanced IFN-β biological activity, prolonged circulating half-life and greater solubility (WO 2006/000448).

Therefore another embodiment is to use such immunoglobulin sequences, for example, Fc fragments of immunoglobulins and variants thereof, as HLEPs. Inhibitors of FXII/FXIIa may be fused to Fc domains or at least portions of immunoglobulin constant regions as HLEPs and may be produced as recombinant molecules in prokaryotic or eukaryotic host cells, such as bacteria, yeast, plant, animal (including insect) or human cell lines or in transgenic animals (WO 2008/098720). A SPINK-K2-Fc fusion protein is exemplarily shown in SEQ ID NO: 7.

Linkers

In one embodiment, an intervening peptidic linker may be introduced between the therapeutic polypeptide and the HLEP. In one embodiment, a cleavable linker is introduced, particularly if the HLEP interferes with the therapeutic polypeptide's specific activity, e.g. by steric hindrance. In certain embodiments, the linker is cleaved by enzymes such as coagulation proteases of the intrinsic, extrinsic, or common coagulation pathway. Coagulation proteases of the intrinsic pathway are proteases in the contact activation pathway, including, for example, FXIIa, FXIa, or FIXa. In one embodiment, the linker is cleaved by FXIIa. Proteases of the extrinsic pathway include proteases in the tissue factor pathway, for example, FVIIa. Proteases of the common pathway include proteases involved in the conversion of fibrinogen to fibrin, for example, FXa, FIIa, and FXIIIa.

Therapeutic Formulation and Administration

The FXII/FXIIa inhibitor or variant thereof may have a purity greater than 80%, or greater than 95%, 96%, 97%, 98%, or 99% purity. In one embodiment, the variant may have a pharmaceutically pure state that is greater than 99.9% pure with respect to contaminating macromolecules, such as other proteins and nucleic acids, and free of infectious and pyrogenic agents.

The purified FXII/FXIIa inhibitor may be dissolved in conventional physiologically compatible aqueous buffer solutions to which there may be added, optionally, pharmaceutical excipients to provide pharmaceutical preparations for treating SBI in a patient. Such pharmaceutical carriers and excipients as well as suitable pharmaceutical formulations are well known in the art. See for example Kibbe et al. Handbook of Pharmaceutical Excipients, (3$^{rd}$ ed., *Pharmaceutical Press*), 2000. The pharmaceutical composition may be formulated in lyophilized or stable soluble form. The polypeptide may be lyophilized by a variety of procedures known in the art. Lyophilized formulations are reconstituted prior to use by the addition of one or more pharmaceutically acceptable diluents such as sterile water for injection or sterile physiological saline solution.

Formulations of the FXII/FXIIa inhibitor are delivered to the patient by any pharmaceutically suitable means of administration. Various delivery systems are known and can be used to administer the composition by any convenient route. The compositions may be administered systemically, such as parenterally. The term "parenteral" as used here includes subcutaneous, intravenous, intramuscular, intra-arterial and intra-tracheal injection, instillation, spray application and infusion techniques. Parenteral formulations may be administered intravenously, either in bolus form or as a constant infusion, or subcutaneously, according to known procedures. Liquid carriers, which are well known for parenteral use, include sterile water, saline, aqueous dextrose, sugar solutions, ethanol, glycols, and oils. For systemic use, the therapeutic proteins may be formulated for an intravenous line or an arterial line. The formulations may be administered continuously by infusion or by bolus injection. Some formulations encompass slow release systems. In one embodiment, the formulation is administered as a patch. Tablets and capsules for oral administration may contain conventional excipients such as binding agents, fillers, lubricants or wetting agents, etc. Oral liquid preparations may be in the form of aqueous or oily suspensions, solutions, emulsions, syrups, elixirs or the like, or may be presented as a dry product for reconstitution with water or other suitable vehicle for use.

Such liquid preparations may contain conventional additives, such as suspending agents, emulsifying agents, non-aqueous vehicles, and preservatives.

The dose of the FXII/FXIIa inhibitor may depend on many factors such as, e.g. the indication, formulation, or mode of administration and may be determined in preclinical and clinical trials for each respective indication. The dose of FXII/FXIIa inhibitor may be administered to a patient before, during, and/or after a medical procedure. In one embodiment, the FXII/FXIIa inhibitor may be administered within 1, 2, 4, 6, 12, 24, 48, 72, or 96 hours before and/or after a medical procedure. A FXII/FXIIa inhibitor may be administered in a single dose, or in multiple doses, or repeatedly in intervals of 0.25, 0.5, 1, 2, 4, 6, 12, 24, or 48 hours before, during and/or after a medical procedure. Because of the advantageous property of not increasing the risk of bleeding, in one embodiment, the FXII/FXIIa inhibitor is administered during the procedure. The pharmaceutical composition may be administered alone or in conjunction with other therapeutic agents. These agents may be co-formulated, or may be administered as separate formulations either concurrently or separately and via the same route of administration or different routes of administration. The schedule of administration or dose of a FXII/FXIIa inhibitor may also vary between individual patients with the same indication or different indications depending on factors such as other medical conditions or therapies.

Another Embodiment are FXII/FXIIa Inhibitors for the Prevention or the Treatment of the Pump Head Syndrome.

The Pump Head syndrome is a central nervous dysfunction or cognitive impairment or cognitive decline after bypass procedures like CABG. Amongst others, it is assumed to be caused by micro-thrombi generated by contact activation at artificial surfaces used in CABG or other medical procedure where blood comes into contact with artificial surfaces. Currently, there is no known therapy for the Pump Head syndrome (Newman et al., NEJM (2001) Vol. 344, No. 6, pp. 394 to 402).

Another embodiment is the use of the above mentioned FXII/FXIIa inhibitors to prevent the blockage of human blood flow in an extracorporeal medical device, which may be by way of non-limiting example a cardiopulmonary bypass device or a device used for the dialysis of blood or the extracorporeal filtration of blood. By "blockage" we mean a reduction of blood flow by at least 10%, at least 20%, at least 30%, at least 40%, at least 50%, at least 60%, at least 70%, at least 80%, at least 90%, at least 95%, at least 99% or a complete cessation of blood flow.

EXAMPLES

1. Laboratory Findings

During a laboratory evaluation recombinant albumin-fused Infestin-4 (rHA-Infestin-4; as described in WO2008/098720) was provided in a syringe and whole blood of a pig was subsequently added. Thereafter this solution was given in a glass vial and clotting time was determined visually by gently shaking the glass vial every minute (incubation at 37° C. in a water bath). Surprisingly, despite the massive contact activation via the glass surface, the blood did not show any signs of clotting up to 3 hours (while control samples clotted after around 3 minutes, FIG. 1). Moreover, subsequent evaluations of activated partial thromboplastin time (aPTT) of this unclotted blood demonstrated prominently prolonged values. These findings encouraged further ex vivo investigations. In these investigations it could be demonstrated that rHA-Infestin-4 dose-dependently prolonged whole blood clotting time (WBCT) (FIG. 1). A comparable profile could be obtained when exemplarily using murine whole blood.

In an additional experiment, a specific anti-FXII/FXIIa antibody was tested in the same study design as explained above. However, since this antibody does not react with porcine system, whole blood from mice was used. Interestingly, although FXII activity is expected to be complete inhibited at the tested doses, WBCT was maximally prolonged around 3 times (FIG. 2). This lead to the conclusion that the prominent effect of rHA-Infestin-4 on WBCT could not only be explained via its FXII/FXIIa inhibitory potential. Instead other mechanisms, perhaps its weaker FXa inhibitory potential, lead to this phenomenal finding.

2. Preclinical Animal Studies 2.1. Data on Animals and Anesthesia
Animal:
Castrated male pigs (large white×German noble) weighing 24-40 kg were procured from a local breeding farm (Willi Schlosser, Schwalmtal, Germany) at age 3-4 months. The animals were housed at 18-21° C. in stables with straw bedding under ambient day-night cycles and fed ad libitum with Deuka V pig chow (Deutsche Tiernahrung Cremer GmbH & Co. KG, DOsseldorf, Germany). Tap water was supplied ad libitum. Animal husbandry and study procedures complied with the German Animal Welfare law and European Union regulations.
Anesthesia:
After an overnight fast with unrestricted access to water the animals were sedated with an intramuscular premedication using a mixture of 2 mg kg-1 azaperone (Stresnil®, Janssen-Cilag GmbH, Neuss, Germany), 15 mg kg-1 ketamine (Ketavet, Pharmacia & Upjohn, Erlangen, Germany) and 0.02 mg kg-1 atropine sulfate (Atropinsulfate, B. Braun Melsungen AG, Melsungen, Germany), the pigs were then anaesthetized with 10 mg kg-1 thiopental sodium via an ear vein. After the surgical preparation of the trachea the animals were intubated, respiration was supported via a Heyer Access ventilator. Inhaled anaesthesia was maintained with 1-2% isoflurane (Isofluran CP®, CP Pharma GmbH, Burgdorf, Germany). A 1.4×2.1 mm catheter was advanced into a carotid artery for collection of blood samples and a 0.5×0.9 mm catheter into a femoral artery for continuous blood pressure measurements. Ringer's solution at 4 mL kg-1 h-1 to satisfy basal fluid requirements and test fluids were infused via an indwelling 1.4×2.1 mm catheter in an external jugular vein. Body temperature was monitored by rectal thermometry.

2.2. Pharmacokinetic Investigations in Pigs
Following the above-mentioned initial laboratory findings, kinetics of a single intravenous (i.v.) rHA-Infestin-4 application were evaluated in pigs. We found that the ex vivo WBCT was markedly prolonged after the single i.v. administrations of rHA-Infestin-4 and decreased again during the elimination of rHA-Infestin-4 from circulation (FIG. 3). In addition, the i.v. administration of rHA-Infestin-4 in pigs led to a dramatic prolongation of aPTT as well as, at high doses, a marginally prolonged prothrombin time (PT) (FIGS. 4 and 5). These results demonstrated that rHA-Infestin-4 influences mainly the intrinsic coagulation pathway (aPTT) as well as, at higher doses, slightly the extrinsic coagulation pathway (PT). Furthermore a prolongation of the clotting time in thrombelastography could be detected.

Interestingly, although WBCT and aPTT was markedly prolonged, skin bleeding time (i.e. physiological hemostasis) was unaffected (FIG. 6).

2.3. Cardiopulmonary Bypass Surgery in the Pig:
In order to evaluate and prove the anticoagulant effect of rHA-Infestin-4 during cardiopulmonary bypass (CPB) procedures, a preclinical CPB trial was performed in a pig model. Primarily the CPB was loaded with rHA-Infestin-4 (corresponding to 50 mg/kg body weight (BW)), and the animal itself was treated with rHA-Infestin-4 at a dose of 200 mg/kg BW before connecting to the CPB device in order to prevent clotting and consecutive occlusion of the oxygenator membrane of the CPB device. No other substances like heparin, or bivalirudin (A. Koster et al. Am J Cardio 2004; 93:356-359) were used as anticoagulant substances.

2.3.1. CPB Study Design:
See FIG. 7 for an Overview about Study Design.
After induction of anesthesia (2.1), sternotomy was performed with an oscillating saw, and the heart was exposed. The pericardium was opened longitudinally and secured via sutures to the chest wall. A purse-string suture was placed right atrium and the cardiac apex. An i.v. infusion of 200 mg/kg BW rHA-Infestin-4 was administered. After ~10 min, a 5.2 mm diameter arterial catheter and a 32 Fr venous catheter were placed in the right atrium and the left ventricle and secured with the tourniquet. Both catheters were connected to a small adult hollow fibre oxygenator with a hard shell venous reservoir (D905 EOS, Sorin SpA, Milan, Italy). The extracorporeal circuit was primed with a solution consisting of 500 mL isotonic saline, 1000 mL 6% hydroxyethyl starch 200/0.5 (Infukoll, Schwarz Pharma AG, Mannheim, Germany), 2 mL kg-1 15% mannitol (Osmofundin®, B. Braun) and 50 mg/kg BW rHA-Infestin-4. The venous and arterial lines were opened in succession and the venous blood allowed to flow into the venous reservoir by gravity. A pump conveyed the blood into the oxygenator. The oxygenated blood was equilibrated to target temperature and returned via the arterial line to the left ventricle. Hypothermia was maintained at 25° C. for 2 hours followed by 1 hour of rewarming to normothermia (37° C.).

Upon termination of CPB, the blood remaining in the oxygenator was returned to the animal. The anticoagulation was not reversed after the CPB procedure.

Blood samples for laboratory assays were collected at (1) baseline, (2) after the infusion of rHA-Infestin-4 but before the commencement of CPB, (3) directly after the commencement of the CPB and (4) later on every 5 min. until the end of the experiment. The skin bleeding time (SBT), defined as the time until cessation of blood loss from a standardized 5 mm long by 1 mm deep inner ear incision created using a Surgicutt® cutting device (International Technidyne Corp., Edison, N.J., USA) was also investigated.

2.3.2. Laboratory Findings During CPB:
During CPB aPTT values were markedly prolonged during the whole study period compared to baseline values (FIG. 8) whereas PT values were only mildly increased during study period (FIG. 9). In addition, also ex vivo WBCT was prominently increased during study period (FIG. 10).

2.3.3. Clinical Findings During CPB:
It is generally known in the medical domain that the direct contact of blood with an artificial surface immediately leads to an activation of coagulation (intrinsic pathway) as well as a direct activation of platelets with consecutive closure of the oxygenator membrane. Therefore the use of heparin during the CPB is currently the gold standard of care.

In house animal (porcine) experiments with the use of 300 IU/KG BW heparin have a higher risk for bleeding as reflected by the prolongation of the SBT as well as bleeding through wound edges.

In contrast to these findings with heparin, the SBT as global test for the risk of bleeding remained unchanged when rHA-Infestin-4 was used in the CPB and furthermore, hemostasis was not impaired when inspecting the wound edges for increased bleeding. However, the most important finding was that the oxygenator of the CPB did not clot and remained fully functional during the test period.

The combination of the surrogate laboratory findings (aPTT, PT), the clinical CPB and SBT results surprisingly show that rHA-Infestin-4 meets the unmet medical need of an novel anticoagulant drug that does not compromise the patients overall ability to form a stable clot whilst the blood remains fully unclotted during procedures that call for artificial surfaces.

3. Conclusion rHA-Infestin-4 was able to prevent clotting of the CBP oxygenator by influencing mainly the intrinsic coagulation pathway, which is reflected in the aPTT, while the extrinsic pathway (PT evaluations) remains unaffected to a certain degree/dose of rHA-Infestin-4. These results were surprising and offer a novel strategy in anticoagulant therapy during CPB since it is not necessary to inhibit the extrinsic and intrinsic coagulation system via heparin/bivalirudin with the increased risk for bleeding. Further on, the remaining risk for microthrombosis and embolization processes during and after CPB procedures might be decreased to a certain level. This novel treatment in CPB procedures shows for the first time that a FXII/FXIIa inhibitor like rHA-Infestin-4 could replace or at least reduce heparin/bivalirudin in the future clinical use resulting in a significantly improved therapeutic opportunity.

4. Further Investigations 4.1. FXII/FXIIa inhibitors are tested in a novel study setup where rabbit whole blood is routed to a cardiopulmonary bypass (CPB) circuit ex vivo. Herein, the blood constantly circulates through the circuit (and not going back into the rabbit) where it encounters massive (contact) activation of the coagulation system if not anticoagulated. This model is used to test the efficacy of FXII/FXIIa inhibitors or combinations of FXII/FXIIa inhibitors and heparin to prevent occlusion of the CPB circuit.

Readouts are amongst others: Pre- and post-oxygenator pressure, complete blood count including platelet count and size, patency of the oxygenator and filters, further readouts of the function of the coagulation system, complement system and kinin-kallikrein system.

We assume that FXII/FXIIa inhibitors are able to prevent occlusion/clotting of the CPB in this ex vivo setup and furthermore are able to reduce the activation of the complement system and kinin-kallikrein system.

4.2. In another set of studies, the effect of FXII/FXIIa inhibitors (rHA-Infestin-4 and the FXII/FXIIa MAb) on human ex vivo whole blood clotting (from healthy donors) is studied. Here, the WBCT is measured as described above (i.e. for pig/mice whole blood) following spiking of different concentrations of the FXII/FXIIa inhibitors. Additionally WBCT can be measured using an ACT (activated clotting time) device. We assume that in line with findings in other species mentioned above, we observe a dose-dependent inhibition of whole blood clotting times ex vivo. The dose of FXII/FXIIa inhibitors, which is needed to achieve equivalent efficacy in the parameters named above (WBCT) compared to a standard dose of unfractionated heparin, will be determined. Additionally, also combinations of FXII/FXIIa inhibitors and low-dose heparin (or other antithrombotic drugs) are tested.

4.3. Furthermore, effects of FXII/FXIIa inhibitors as well as combinations of FXII/FXIIa inhibitors and heparin (or other antithrombotic drugs) are tested in an ex vivo circuit system (human whole blood from healthy drug free donors is routed into the system while the drugs are already provided in the system) comprised of either a standard CPB system, a standard ECMO system, or another clinically-relevant ex vivo circuit. Herein, the blood is constantly circulating in the circuit (and not brought back into the donor) where it encounters massive (contact) activation of the coagulation system. Readouts are amongst others: Pre- and post-oxygenator pressure, complete blood count including platelet count and size, patency of the oxygenator and filters, further readouts of the function of the coagulation system, complement system and kinin-kallikrein system. It is assumed that, FXII/FXIIa inhibitors or combinations of FXII/FXIIa inhibitors and low-dose heparin (or other antithrombotic drugs) are also able to prevent clotting of the circuit. Furthermore, it is assumed that FXII/FXIIa inhibitors are able to reduce the activation of the complement system and kinin-kallikrein-system within this ex vivo circuit. The dose of FXII/FXIIa inhibitors, which needed to achieve equivalent efficacy in the parameters and readouts named above compared to a standard dose of unfractionated heparin, will be determined.

This novel approach to the treatment of patients before, during and/or after contact activation of the coagulation system provides protection of thrombosis before, during and/or after certain procedures, while the patient is not put on risk for bleeding events at the same time.

---

The invention claimed is:

1. A method of preventing or reducing a risk of thrombi formation or stabilization of formed thrombi in a human or animal subject during and/or after a medical procedure, comprising
   (A) administering to the subject an inhibitor of FXII/FXIIa before and/or during and/or after the medical procedure in an amount sufficient to prevent or reduce the risk of thrombi formation or stabilization during and/or after the medical procedure,
   (B) administering to the subject heparin or a derivative thereof and/or hirudin or a derivative thereof before and/or during and/or after the medical procedure, and
   (C) contacting blood of the subject with an artificial surface, wherein the artificial surface
      (i) is exposed to at least 80% of the blood volume of the subject and the artificial surface is at least 0.2 m²,
      (ii) is a container for collection of blood outside the body of the subject, and/or (iii) is a stent, valve, intraluminal catheter, or a system for internal assisted pumping of blood,
   wherein the amount of heparin or derivative thereof and/or hirudin or derivative thereof is reduced compared to the amount administered before and/or during and/or after the medical procedure when no inhibitor of FXII/FXIIa is administered.

2. The method of claim 1, wherein the medical procedure comprises one or more of
   i) a cardiopulmonary bypass,
   ii) oxygenation and pumping of blood via extracorporeal membrane oxygenation,
   iii) assisted pumping of blood (internal or external),
   iv) dialysis of blood,
   v) extracorporeal filtration of blood,
   vi) collection of blood from the subject in a repository for later use in an animal or a human subject,
   vii) use of venous or arterial intraluminal catheter(s),
   viii) use of device(s) for diagnostic or interventional cardiac catherisation,
   ix) use of intravascular device(s),
   x) use of artificial heart valve(s), and
   xi) use of artificial graft(s).

3. The method of claim 2, wherein the medical procedure comprises a cardiopulmonary bypass.

4. The method of claim 2, wherein the medical procedure comprises collection of blood from the subject in a repository for later use in an animal or human subject.

5. The method of claim 1, wherein the inhibitor is administered to the subject by:
   i) administration to the subject before and/or during collection of blood from the subject,
   ii) mixing the inhibitor with blood from a repository and administering the resulting mixture to the subject, and/or
   iii) administering the inhibitor to the subject before, during, and/or after administration of blood to the subject.

6. The method of claim 1, wherein the FXII/FXIIa inhibitor is administered by being coated on the artificial surface.

7. The method of claim 1, wherein said human or animal subject has a reduced or no prothrombotic risk after the medical procedure.

8. The method of claim 1, wherein said human or animal subject has a reduced or no prothrombotic risk following a postoperative antagonism of heparin or derivatives thereof and/or a postoperative antagonism of hirudin or derivatives thereof.

9. The method of claim 1, further comprising administering a heparin and/or hirudin antagonist after the medical procedure, wherein the amount of the antagonist administered to the subject is reduced compared to the amount of said antagonist administered after said medical procedure when no inhibitor of FXII/FXIIa is administered.

10. The method of claim 1, wherein the subject suffers from or is at risk of developing Pump Head syndrome.

11. The method of claim 1, wherein the FXII/FXIIa inhibitor comprises
   (i) wild type Infestin-4 polypeptide sequence (SEQ ID NO: 1), or a variant thereof, wherein a variant comprises
      (a) amino acids 2-13 of the wild type Infestin-4 sequence (SEQ ID NO: 1), and at least one and up to five amino acid mutations outside of amino acids 2-13 that result in differences from the wild type Infestin-4 sequence; and/or
      (b) six conserved cysteine residues from the wild type Infestin-4 sequence (SEQ ID NO: 1), and a homology of at least 70% to the wild type Infestin-4 sequence,
   (ii) SPINK-1 (SEQ ID NO:2), which is mutated to include N-terminal amino acids 2-13 of the wild type Infestin-4 sequence (SEQ ID NO: 1), or a variant of said mutated SPINK-1, wherein the variant comprises
      (a) N-terminal amino acids 2-13 of the wild type Infestin-4 sequence (SEQ ID NO: 1); and at least one and up to five amino acid mutations outside said N-terminal amino acids that result in differences from the wild type SPINK-1 sequence and which increase the homology of the variant to the wild type Infestin-4 sequence; and/or
      (b) six conserved cysteine residues from the wild type SPINK-1 sequence and a homology of at least 70% to the wild type SPINK-1 sequence,
   (iii) antithrombin III (AT III), angiotensin converting enzyme inhibitor, C1 inhibitor, aprotinin, alpha-1 protease inhibitor, antipain ([(S)-1 Carboxy-2-Phenyl-ethyl]-Carbamoyi-L-Arg-L-Vai-Arginal), Z-Pro-Pro-aldehyde-dimethyl acetate, DX88, leupeptin, Fmoc-AlaPyr-CN, corn-trypsin inhibitor (CTI), mutants of the bovine pancreatic trypsin inhibitor, ecotin, YAP (yellowfin sole anticoagulant protein), *Cucurbita maxima* trypsin inhibitor-Y, Curcurbita maxima isoinhibitors, and/or Pro-Phe-Arg-chloromethyl-ketone (PCK); or
   (iv) an anti-FXII/FXIIa antibody, wherein the antibody binds to FXII/FXIIa and inhibits its activity and/or activation.

12. The method of claim 1, wherein the FXII/FXIIa inhibitor comprises SPINK K1, K2, or K3 (SEQ ID NO: 3, 4, or 5).

13. The method of claim 1, wherein the FXII/FXIIa inhibitor is linked to a half-life enhancing polypeptide, wherein the half-life enhancing peptide comprises albumin, afamin, alpha-fetoprotein or vitamin D binding protein, human albumin, or a variant thereof, an immunoglobulin or variant thereof, or an Fc of an IgG.

14. The method of claim 13, wherein the half-life enhancing polypeptide is linked to the FXII/FXIIa inhibitor via a linker.

15. The method of claim 14, wherein the linker is at least one of:
   (i) cleavable;
   (ii) cleavable by a coagulation protease of the intrinsic, extrinsic, or common coagulation pathway; and
   (iii) cleavable by FXIIa.

16. The method of claim 1, wherein heparin or derivative thereof and/or hirudin or derivative thereof is administered at the same time as the inhibitor of FXII/FXIIa.

17. The method of claim 1, wherein heparin or derivative thereof and/or hirudin or derivative thereof is administered before or after the inhibitor of FXII/FXIIa.

* * * * *

SEQUENCE LISTING

<160> NUMBER OF SEQ ID NOS: 7

<210> SEQ ID NO 1
<211> LENGTH: 48
<212> TYPE: PRT
<213> ORGANISM: Trioma infestans

<400> SEQUENCE: 1

```
Glu Val Arg Asn Pro Cys Ala Cys Phe Arg Asn Tyr Val Pro Val Cys
1               5                   10                  15

Gly Ser Asp Gly Lys Thr Tyr Gly Asn Pro Cys Met Leu Asn Cys Ala
            20                  25                  30

Ala Gln Thr Lys Val Pro Gly Leu Lys Leu Val His Glu Gly Arg Cys
        35                  40                  45
```

```
<210> SEQ ID NO 2
<211> LENGTH: 56
<212> TYPE: PRT
<213> ORGANISM: Homo sapiens

<400> SEQUENCE: 2

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 3
<211> LENGTH: 53
<212> TYPE: PRT
<213> ORGANISM: Artificial sequence
<220> FEATURE:
<223> OTHER INFORMATION: Mutated human SPINK-1

<400> SEQUENCE: 3

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
        35                  40                  45

Lys Ser Gly Pro Cys
    50

<210> SEQ ID NO 4
<211> LENGTH: 53
<212> TYPE: PRT
<213> ORGANISM: Artificial sequence
<220> FEATURE:
<223> OTHER INFORMATION: Mutated human SPINK-1

<400> SEQUENCE: 4

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Cys Ala Glu Asn Arg Lys Arg Gln Thr Ser Ile Leu Ile Gln
        35                  40                  45

Lys Glu Gly Pro Cys
    50

<210> SEQ ID NO 5
<211> LENGTH: 54
<212> TYPE: PRT
<213> ORGANISM: Artificial sequence
<220> FEATURE:
<223> OTHER INFORMATION: Mutated human SPINK-1

<400> SEQUENCE: 5

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30
```

```
Met Leu Asn Cys Ala Glu Asn Arg Lys Arg Gln Thr Ser Ile Leu Ile
             35                  40                  45

Gln Lys Glu Gly Pro Cys
 50
```

<210> SEQ ID NO 6
<211> LENGTH: 585
<212> TYPE: PRT
<213> ORGANISM: Homo sapiens

<400> SEQUENCE: 6

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350
```

```
Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 7
<211> LENGTH: 294
<212> TYPE: PRT
<213> ORGANISM: Artificial Sequence
<220> FEATURE:
<223> OTHER INFORMATION: Fusion Protein

<400> SEQUENCE: 7

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Cys Ala Glu Asn Arg Lys Arg Gln Thr Ser Ile Leu Ile Gln
        35                  40                  45

Lys Glu Gly Pro Cys Gly Gly Ser Gly Gly Ser Gly Gly Ser Glu Pro
    50                  55                  60

Lys Ser Cys Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125
```

```
Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
    290
```